United States Patent [19]

Rosenberg et al.

[11] Patent Number: 5,571,686
[45] Date of Patent: Nov. 5, 1996

[54] METHOD OF USING MEGAPOIETIN FOR PROLONGING THE SURVIVAL & VIABILITY OF PLATLETS

[75] Inventors: Robert D. Rosenberg, Jamestown, R.I.; David J. Kuter, Reading; David Beeler, Cambridge, both of Mass.

[73] Assignee: Massachusetts Institute of Technology, Cambridge, Mass.

[21] Appl. No.: 227,530

[22] Filed: Apr. 14, 1994

[51] Int. Cl.$^6$ ............................ A61K 38/19; C07K 14/52
[52] U.S. Cl. .............................. 435/29; 424/85.1; 514/2; 514/8; 514/12; 514/885
[58] Field of Search ............................ 424/85.1; 435/29; 514/2, 8, 12, 885

[56] References Cited

U.S. PATENT DOCUMENTS 5,260,417  11/1993  Grant et al. .............................. 530/351

OTHER PUBLICATIONS

Mazun et al. (1981), Journal of Clinical Investigation, vol. 68, pp. 733–741.

Bartley, T. D. et al. "Identification and Cloning of a Megakaryocyte Growth and Development Factor That Is a Ligand for the Cytokine Receptor Mpl" *Cell* 77: 1117–1124 (1 Jul. 1994).

de Sauvage, F. et al. "Stimulation of megakaryocytopoiesis and thrombopoiesis by the c–Mpl ligand" *Nature* 369: 533–538 (16 Jun. 1994).

Kaushansky, K. et al. "Promotion of megakaryocyte progenitor expansion and differentiation by the c–Mpl ligand thrombopoietin" *Nature* 369: 568–571 (16 Jun. 1994).

Kuter, D. J. and R. D. Rosenberg "Appearance of a Megakaryocyte Growth–Promoting Activity, Megapoietin, During Acute Thrombocytopenia in the Rabbit" *Blood* 84(5): 1454–1472 (1 Sep. 1994).

Kuter, D. J. et al. "The purification of megapoietin: A physiological regulator of megakaryocyte growth and platelet production" *Proc. Natl. Acad. Sci. USA* 91: 11104–11108 (Nov. 1994).

Lok, S. et al. "Cloning and expression of murine thrombopoietin cDNA and stimulation of platelet production *in vivo*" *Nature* 369: 565–568 (16 Jun. 1994).

Wendling, F. et al. "c–Mpl ligand is a humoral regulator of megakaryocytopoiesis" *Nature* 369: 571–574 (16 Jun. 1994).

Radek C. Skoda, David C. Seldin, Ming–Ko Chiang, Catherine L. Peichel, Thomas F. Vogt and Philip Leder, "Murine c–mpl: a member of the hematopoietic growth factor receptor superfamily that transduces a proliferative signal", *The EMBO Journal*, vol. 12, No. 7, pp. 2645–2653 (1993).

Nassia Methia, Fawzia Louache, William Vainchenker and Francoise Wendling, "Oligodeoxynucleotides Antisense to the Proto–oncogene c–mpl Specifically Inhibit In Vitro Megakaryocytopoiesis", *Blood*, vol. 82, No. 5, pp. 1395–1401 (Sep. 1, 1993).

Ronald J. Hill, Jack Levin and Francine C. Levin, "Correlation of in vitro and in vivo Biological Activities During the Partial Purification of Thrombopoietin", *Experimental Hematology*, vol. 20, pp. 354–360 (1992).

Isabelle Vigon, Jean–Paul Mornon, Laurence Cocault, Marie–Therese Mitjavila, Pierre Tambourin, Sylvie Gisselbrecht and Michele Souyri, "Molecular cloning and characterization of MPL, the human homolog of the v–mpl oncogene: Identification of a member of the hematopoietic growth factor receptor superfamily", *Proc. Natl. Acad. Sci. USA*, vol. 89, pp. 5640–5644 (Jun. 1992).

David J. Kuter, Dianne M. Gminski and Robert D. Rosenberg, "Transforming Growth Factor β Inhibits Megakaryocyte Growth and Endomitosis", *Blood*, vol. 79, No. 3, pp. 619–626 (Feb. 1, 1992).

Neil Williams, "Is Thrombopoietin Interleukin 6?", *Experimental Hematology*, vol. 19, pp. 714–718 (1991).

Michele Souyri, Isabelle Vigon, Jean–Francois Penciolelli, Jean–Michel Heard, Pierre Tambourin and Francoise Wendling, "A Putative Truncated Cytokine Receptor Gene Transduced by the Myeloproliferative Leukemia Virus Immortalizes Hematopoietic Progenitors", *Cell*, vol. 63, pp. 1137–1147 (Dec. 21, 1990).

David J. Kuter and Robert D. Rosenberg, "Regulation of Megakaryocyte Ploidy In Vivo in the Rat", *Blood*, vol. 75, No. 1, pp. 74–81 (Jan. 1, 1990).

Julio E. Celis, Gitte P. Ratz, Peder Madsen, Borbala Gesser, Jette B. Lauridsen, Sianette Kwee, Hanne Holm Rasmussen, Henrik V. Nielsen, Dorthe Cruger, Bodil Basse, Henrik Leffers, Bent Honore, Olaf Moller, Ariana Celis, Joel Vanderkerckhove, Guy Bauw, Jozef van Damme, Magda Puype and Marc Van den Bulcke,"Comprehensive, human cellular protein databases and their implication for the study of genome organization and function", *FEBS LETTERS*, vol. 244, No. 2, pp. 247–254 (Feb. 1989).

David J. Kuter, Sheryl M. Greenbeg and Robet D. Rosenberg, "Analysis of Megakaryocyte Ploidy in Rat Bone Marrow Cultures", *Blood*, vol. 74, No. 6, pp. 1952–1962 (Nov. 1, 1989).

T. P. McDonald, "Thrombopoietin: Its Biology, Purification and Characterization", *Experimental Hematology*, vol. 16, pp. 201–205 (1988).

(List continued on next page.)

Primary Examiner—Garnette D. Draper
Assistant Examiner—Prema Mentz
Attorney, Agent, or Firm—Lahive & Cockfield

[57] ABSTRACT

New therapies for treating blood platelet disorders based on the megapoietin gene and protein are described. Additional utilities for megapoietin such as increasing the storage life of platelet and whole blood preparations, a means for selectively targeting therapeutic or imaging agents to arterial clots, and a means for selectively stimulating platelet production from megakaryocytes in vivo and in vitro (e.g., as a source of platelets for transplantation) and to stimulate stem cell growth are also described.

4 Claims, 2 Drawing Sheets

OTHER PUBLICATIONS

Guy Tayrien and Robert D. Rosenberg, "Purification and Properties of a Megakaryocyte Stimulatory Factor Present Both in the Serum–free Conditioned Medium of Human Embryonic Kidney Cells and in Thrombocytopenic Plasma", *The Journal of Biological Chemistry*, vol. 262, No. 7, pp. 3262–3268 (1987).

Sheryl M. Greenberg, David J. Kuter and Robert D. Rosenberg, "In Vitro Stimulation of Magakaryocyte Maturation by Megakaryocyte Stimulatory Factor", *The Journal of Biological Chemistry*, vol. 262, No. 7, pp. 3269–3277 (1987).

Bertram Spector, "In vivo Transfer of a Thrombopoietic Factor", *P.S.E.B.M.*, vol. 108 (1961).

International Search Report (Form PCT/ISA/220) for PCT/US95/04617 mailed on Jul. 12, 1995.

McDonald et al., "A Four–Step Procedure for the Purification of Thrombopoietin", *Experimental Hematology*, vol. 17, pp. 865–871 (1989).

Vannucchi et al., "Partial Purification and Biochemical Characterization of Human Plasma Thrombopoietin", *Leukemia*, vol. 2, No. 4, pp. 236–239 (Apr. 1988).

Zeigler et al., "In Vitro Megakaryocytopoietic and Thrombopoietic Activity of c–mpl Ligand (TPO) on Purified Murine Hematopoietic Stem Cells", *Blood*, vol. 84, No. 12, pp. 4045–4052 (Dec. 1994).

METHOD OF USING MEGAPOIETIN FOR PROLONGING THE SURVIVAL & VIABILITY OF PLATLETS

GOVERNMENT SUPPORT

Work described herein has been supported, in part, by NIH Grant No. HL39753. The U.S. Government may therefore have certain rights in the invention.

BACKGROUND OF THE INVENTION

Blood platelets are required for the maintenance of normal hemostasis. Platelets initiate blood clot formation and release growth factors that speed the process of wound healing as well as potentially serving other functions. Platelets are the terminal differentiation product of megakaryocytes, which in turn originate from pluripotent stem cells of the bone marrow. The maturation and differentiation processes that begin with pluripotent stem cells and end with blood platelets are complex and incompletely understood. However, it is thought that humoral factors influence different cellular steps in megakaryocyte development.

A number of diseases or conditions result frown inappropriate levels or inadequate function of blood platelets. For example,"thrombocytopenias" are the result of an abnormally small number of platelets in the circulating blood. Thombocytopenia can be due to antibody mediated platelet destruction (Karpatkin, S., *Sem in Hematol.*, 22:260–288 (1985)), massive blood transfusions, cardio-pulmonary bypass or bone marrow failure from malignant infiltration, aplastic anemia or chemotherapy (Heyman, M. R., and C. A. Schiffer, *Sem. Onc.*, 17:198 (1990)). "Thrombocythemic" disorders, on the other hand, are the result of a high platelet count. Finally, "thrombocytopathic" blood disorders are characterized by abnormally low or high platelet function, although platelet counts may be normal.

Platelet disorders are clinically managed primarily by whole blood or platelet transfusions. However, blood and platelet supplies can become limited. Also, storage of platelet and whole blood preparations can be problematic. For example, it has been found that normal human platelets have a "shelf-life" of approximately 5 days. In addition, transfusions can transmit infection and are costly. Further patients are often refractory to subsequent transfusions. In view of the problems associated with available therapies, many researchers have been working to identify, humoral factors involved with platelet generation, which would be clinically useful. Although a number of putative megakaryocyte growth promoting factors have been identified to date (e.g., thrombopoietin (Hill, R. J. et. al., *Exp. Hematol.* 20:354 (1992)); thrombopoietic stimulatory factor (McDonald, T. P. *Exp, Hematol.* 16:201 ( 1988)); megakaryocyte stimulatory factor (Tayrien, G. et. al., *J. Biol,.Chem,.* 262:3262 (1987), and Greenberg, S. M. et. al., *J. Biol. Chem.* 262:3269 (1987)) Il-1 (Monroy, RL et. al., *Exp Hematol.* 9:629 (1991)); Il-6 (Williams, N. *Exp. Hematol.* 19:714 (1991)); Il-11 (Goldman, SJ et. al., *Blood* 80:91a (1992)); and erythropoietin (Berridge, MV et. al., *Blood* 72:970 (1988)), none has been shown to possess all of the physiological properties expected of a humoral stimulator of platelet production (i.e., low basal levels; circulating levels which vary reciprocally and proportionally to changes in platelet mass; lag period before the level of the circulating factor changes in response to alterations in the platelet mass; and suppression of the levels of the factor following platelet transfusion).

Isolation of a true "megakaryocyte growth promoting factor" would be useful for treating blood platelet disorders.

SUMMARY OF THE INVENTION

In one aspect, the instant invention features new therapies for treating or preventing blood platelet disorders which are based on the isolation and characterization of a humoral megakanyocyte growth promoting factor called "megapoietin". In one embodiment, the instant invention features megapoietin and therapeutic compositions of megapoietin that stimulate an increase in the number, size and ploidy of megakaryocytes in vitro or when administered to a subject in vivo and increases the number and size of platelets in vivo. In a preferred embodiment, the megapoietin is a 31 kd protein as determined by SDS gel electrophoresis under reducing conditions and is 28 kd as determined by SDS gel electrophoresis under nonreducing conditions.

In another aspect, the invention relates to methods for making the disclosed megapoietin protein and therapeutic compositions comprising the protein. In a preferred embodiment, the megapoietin is made by recombinant means, for example by culturing recombinant cells encoding the protein, so that megapoietin is expressed and can be isolated. Alternatively, recombinant megapoietin is produced in transgenic animals, which have been engineered to encode heterologous megapoietin. Preferably recombinant megapoietin is expressed and isolated from a transgenic animal in a manner that is not detrimental to the animal's own health. In further embodiments, megapoietin is purified from natural sources or is chemically synthesized. The invention also relates to anti-megapoietin antibodies, methods for making the antibodies and various research, diagnostic and therapeutic uses therefor.

In a further aspect, the invention relates to genes encoding megapoietin proteins and use of the genes, for example, in making recombinant megapoietin proteins, in making probes for use in diagnosing platelet disorders and use of the genes and antisense molecules made from the genes in gene therapy protocols.

In still another aspect, the invention relates to "alternative therapies" for treating a platelet disorder based on what is known of the normal mechanism for megapoietin production and regulation. For example, in one embodiment, the invention features agents (e.g., transcription factors or other small molecules) capable of increasing the production (e.g., expression) of a subject's endogenous functional megapoietin genes and thereby producing increased levels of megapoietin in the subject. In another embodiment, the invention relates to antibodies, small molecules or megapoietin antagonists capable of blocking the binding and removal of endogenous megapoietin to platelet megapoietin receptors.

Protein-based, gene therapy or alternative megapoietin-based procedures and composition for treating or preventing blood platelet disorders are preferable to current transfusion therapies, which are vehicles for infection (e.g., hepatitis and AIDS), are plagued by inadequate supplies and often result in refactoriness to subsequent platelet transfusions. In addition, because megapoietin exhibits all of the physiological characteristics expected of an endogenous regulator of platelet production, megapoietin is far more useful clinically (i.e., safe and effective) than previously identified, putative megakaryocyte growth promoting factors.

Other features of the instant invention relate to the use of megapoietin as: i) an additive to whole blood or platelet supplies to enhance storage life (e.g., prior to transfusion);

ii) a means for selectively targetting agents (e.g., therapeutic or imaging) to platelets, present, for example, in arterial clots for specifically detecting and treating disorders such as acute myocardial infarction and stroke which are the result of platelet mediated blood clotting; iii) a means for selectively stimulating platelet production in vivo prior to platelet pheresis; iv) a means for non-specifically increasing circulating peripheral stem cells for collection by leukopheresis and subsequent stem cell transplantation; and v) a means for stimulating stem cell growth and/or megakaryocyte number, size, ploidy and platelet production in bone marrow bioreactors. Additional features and advntages of the invention will become apparent from the following detailed description and claims.

DETAILED DESCRIPTION OF THE INVENTION

Figure 1:
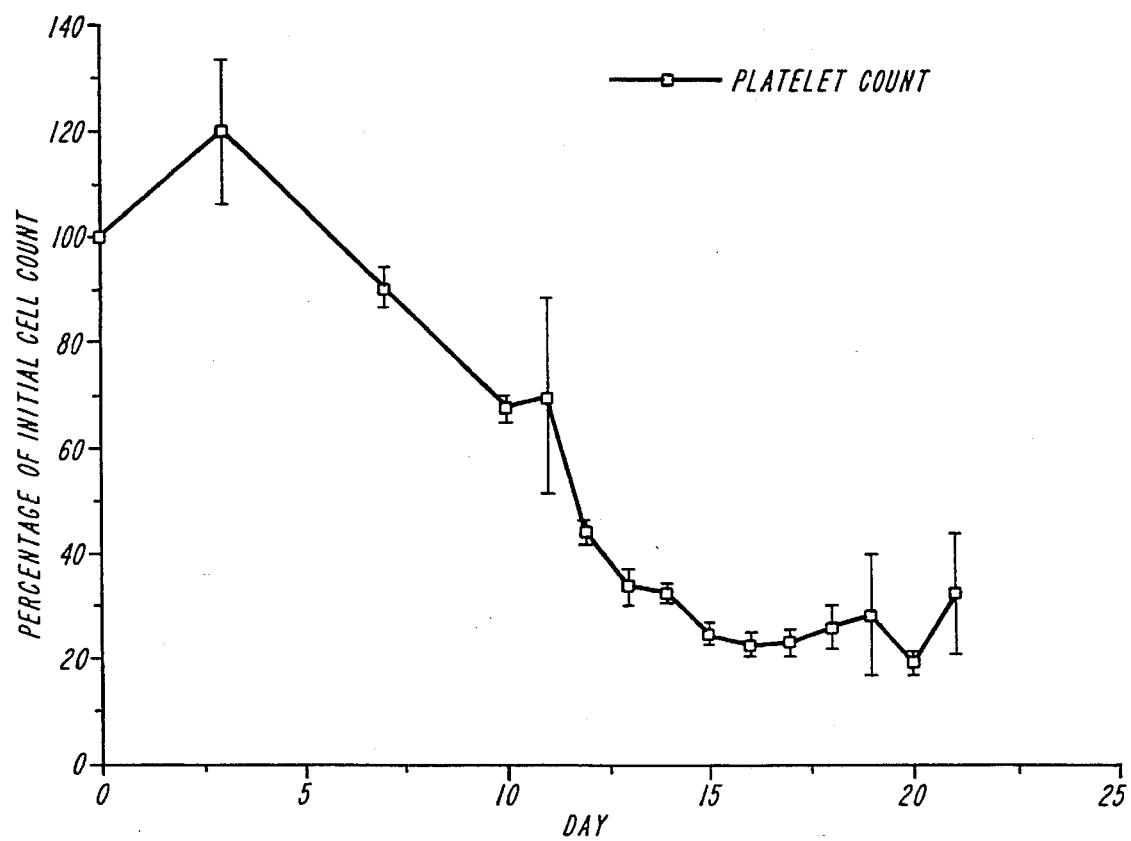
FIG. 1 is a graph plotting the average platelet count over a 22 day period for 106 sheep injected subcutaneously with 900 mg. of busulfan/$m^2$ of body surface area injected subcutaneously on days 0 and 3.

As used herein, the following words and phrases shall have the meanings set forth below:

"megapoietin gene" shall mean genetic material (e.g., DNA or RNA) that carries the information representing or encoding a megapoietin protein.

"megapoietin protein" shall mean a glycosylated or unglycosylated protein, polypeptide or peptide that exhibits the following biological activities: i) stimulates an increase in megakaryocyte size, number and ploidy as well as production of platelets therefrom; and ii) binds to platelets in vitro or in vivo. A preferred megapoietin is about 31 kd as determined by SDS gel electrophoresis under reducing conditions and is about 28 kd under nonreducing conditions.

"platelet disorder" shall mean a condition or disorder caused by a blood platelet dysfunction, or an insufficient or over supply of blood platelets. One category of blood platelet disorders, thrombocytopenias, are characterized by exhibiting a relatively low platelet count. Diseases such as autoimmune, neonatal thrombocytopenia; thrombotic thrombocytopenic purpura; idiopathic (immune) thrombocytopenic purpura; and dilutional thrombocytopenia; as wells as low platelet count conditions resulting from or associated with e.g., aplastic anemia; malignant infiltration; chemotherapy or other bone marrow failure state; bone marrow transplantation; antibody mediated platelet destruction; blood transfusions; cardiopulmonary by-pass; AIDS; disseminated intravascular coagulation; hemolytic uremic syndrome; leukemia; hypersplenism; myelodysplastic disorders and arteriovenous realformations; puhnonary hypertension; kidney graft rejection; and administration of heparin or certain drugs are examples of thrombocytopenic platelet disorders. Another category of blood platelet disorders, thrombocythemias, are characterized by exhibiting a relatively low platelet count. Diseases such as idiopathic thrombocythemia and high platelet count conditions resulting from or associated with e.g., reactive thrombocytosis secondary to inflammation, iron deficiency or malignancy, polycythemia vera, chronic myelogenous leukemia, myeloid metaplasia or any other myeloproliferative condition are examples of thrombocythemic platelet disorders. A final category of blood platelet disorders, thrombocytopathies are characterized by having either an abnormally high or low platelet function, although the platelet levels (count) may be in the normal range. Examples of thrombocytopathic diseases in which platelet function is low include: Mediterranean thrombocytopathy, von Willebrand's disease, and idiopathic (immune) thrombocytopenic purpura. Low platelet function, thrombocytopathic conditions can also be associated with or result from e.g., HIV infection, drug induced or hereditary storage pool disorders, uremia, myelodysplastic disorders, or thrombolytic therapy. Examples of thrombocytopathic diseases in which platelet function is high include essential thrombocythemia. In addition, a thrombocytopathic, high platelet function condition can be associated with or result from myeloproliferative disorders, atherosclerosis, myocardial infarction, unstable angina, and stroke and other vascular thrombosis disorders such as peripheral vascular disease.

"Subject"—shall mean a human or vertebrate animal.

As described in detail in the following examples, megapoietin (MP), a protein having a molecular weight of about 31,000 daltons (31 kd) as determined by SDS gel under reducing conditions and 28,000 daltons (28 kd) under nonreducing conditions, has at last been isolated. Although researchers have been actively searching for this factor for over 10 years, its isolation awaited a novel technique for inducing the thrombocytopenic condition in animals. As described in detail in the attached examples, this technique was used to make over 100 sheep thrombocytopenic prior to obtaining their blood and isolating MP. In vivo and in vitro studies performed with the purified factor and thrombocytopenic plasma containing the factor confirm that megapoietin exhibits all of the physiological properties expected of an endogenous regulator of platelet production. For example, in healthy (non-thrombocytopenic) animals and humans, basal levels are low and may be further suppressed by platelet transfusion. In addition levels of the factor have been found to rise during induction of thrombocytopenia and are inversely proportional to the platelet count. Elevated levels can, however, be suppressed by the transfusion of platelets and indeed it has been shown that platelets bind to and remove megapoietin.

Based on the purified factor, a gene encoding the megapoietin protein can be isolated (e.g., as described in the attached example 6) and introduced (preferably in a suitable expression cassette,containing an appropriate promoter and optional enhancer sequence) into cells in culture using standard techniques (e.g., via calcium phosphate or calcium chloride co-precipitation, DEAE dextran mediated transfection, lipofection, or electroporation). Recombinant cells encoding megapoietin can then be cultured in vitro in a manner that allows expression and preferably also secretion, and the recombinant factor can be purified using well known techniques. Either prokaryotic or eukaryotic cells may be useful "host cells" for producing recombinant megapoietin in vitro. Preferred host cells are mammalian cells (e.g., COS, Baby hamster kidney (BHK) and C127 cells), yeast cells and insect cells.

As an alternative to production by in vitro culture, recombinant megapoietin can also be produced in vivo, for example in a transgenic animal. Preferably in vivo production is carried out in a manner that is not detrimental to the animal host. For example it can be imagined that high levels of megapoietin circulating in an animal's vascular system could result in the formation of blood clots in the animal. Transgenic methods for producing recombinant proteins are well known in the art and include for example production and secretion in mammalian milk (see e.g., U.S. Pat. No. 4,873,316 entitled "Isolation of Exogenous Recombinant Proteins From The Milk of Transgenic Mammals" to Meade et.al.)

Megapoietin can further be purified from mammalian plasma. Thrombocytopenic plasma in which the level of megapoietin is upregulated is a particularly useful source for obtaining purified megapoietin. A particularly useful purification scheme is set forth in the attached example 5. This purification scheme is also useful for isolating recombinant megapoietin from culture media and animal body fluids produced e.g., using the procedures described above. Megapoietin or a functional fragment can also be chemically synthesized using methods that are known in the art.

It may be advantageous to use a functional fragment or derivative of the whole megapoietin protein, for example in developing an appropriate pharmaceutical composition or for generating antibodies. Various fragments and derivatives of megapoietin can be tested for biological activity (i.e., ability to stimulate platelet production by megakaryocytes and to bind to platelets) using an appropriate activity assay (e.g., the flow cytometer or serotonin assays described in the attached examples). In addition, variously glycosylated forms of megapoietin can be tested for example for increased circulatory life using an appropriate activity assay.

A subject can be treated by administration of an "effective amount" of a megapoietin protein alone or in conjunction with a pharmaceutically acceptable carrier or diluent according to any method that allows access into a subject's blood stream and enables contact with the subject's megakaryocytes. An "effective amount" of megapoietin is an amount sufficient to reduce or eliminate the symptoms associated with a platelet disorder. The effective amount can be determined by one of skill in the art using no more than routine experimentation and may take into account such factors as the type and severity of symptoms being treated, the weight and/or age of the subject, the previous medical history of the subject, and the selected route for administration. Exemplary modes of administration include subcutaneously, intravenously, intraperitoneally, intramuscularly, parenterally, submucosally, orally, transdermally or other appropriate manner. If necessitated by a particular mode of administration, a megapoietin protein can be encapsulated within a material that protects it from enzymatic degradation.

Alternatively, a preparation of a megapoietin gene can be incorporated into a suitable vector for delivering the gene to appropriate cells in a subject suspected or known to have a platelet disorder. Since platelet disorders are blood disorders, gene therapy vectors preferably are capable of delivering a megapoietin gene into a subject's stem cells (e.g., in the bone marrow or peripheral blood) or into some other hematopoietic (blood) cell. It may also be useful to administer genes encoding a megapoietin protein to a subject's lungs, as natural megapoietin protein has been found to be concentrated in lung tissue and therefore, lungs may be the primary site of natural megapoietin protein production. For use in clinical treatment, appropriate vectors must also be appropriately maintained in host cells and be safe. Preferred vectors for performing gene therapy include retrovirus, adenovirus, adeno-associated virus and lipid based vectors.

A subject can be treated by administration of an "effective amount" of a gene encoding megapoietin protein alone or in conjunction with a pharmaceutically acceptable carrier or diluent according to any method that allows access into a subject's blood stream and enables contact with the subject's megakaryocytes. An "effective amount" of a megapoietin gene is an amount sufficient to result in manufacture of sufficient megapoietin protein to reduce or eliminate the symptoms associated with a platelet disorder. The effective amount can be determined by one of skill in the art using no more than routine experimentation and may take into account such factors as the type and severity of symptoms being treated, the weight and/or age of the subject, the previous medical history of the subject, and the selected route for administration. Exemplary modes of administration of a megapoietin gene therapy vector include subcutaneously, intravenously, intraperitoneally, intramuscularly, parenterally, submucosally, orally, transdermally or other appropriate manner. If necessitated by a particular mode of administration, a megapoietin gene can be encapsulated within a material that protects it from enzymatic degradation. As an alternative to or in conjunction with gene therapy, a subject can be treated with an agent (e.g., a transcription factor or other small molecule) capable of increasing the production (e.g., expression) of a subject's endogenous, functional megapoietin genes and thereby producing increased levels of megapoietin in the subject. Such an agent can be prepared as a pharmaceutical composition and administered to a subject in an appropriate manner.

Thrombocythemias or thrombocytopathies resulting from high platelet count or function can be treated using "antisense" nucleic acid fragments that are complementary to a megapoietin gene. A subject can be treated by administration of an "effective amount" of an antisense megapoietin gene alone or in conjunction with a pharmaceutically acceptable carrier or diluent according to any method that allows access into a subject's blood stream. An "effective amount" of an antisense megapoietin gene is an amount sufficient to inhibit manufacture of sufficient megapoietin protein or protein function or to reduce or eliminate the symptoms associated with a platelet disorder. The effective amount can be determined by one of skill in the art using no more than routine experimentation and may take into account such factors as the type and severity of symptoms being treated, the weight and/or age of the subject, the previous medical history of the subject, and the selected route for administration. Exemplary modes of administration of an antisense megapoietin gene therapy vector include subcutaneously, intravenously, intraperitoneally, intramuscularly, parenterally, submucosally, orally, transdermally or other appropriate manner. If necessitated by a particular mode of administration, an antisense megapoietin gene can be encapsulated within a material that protects it from enzymatic degradation.

In addition to being useful for treating platelet disorders, megapoietin proteins and encoding genes may be used as additives to increase the shelf-life of platelet and whole blood preparations. The normal survival time for platelets is estimated to be less than one week. However, by adding a megapoietin protein to a platelet containing preparation (e.g., whole blood or a platelet preparation), it has been found (see example 9) that platelet survival rate can be increased at least 9 fold. In addition to being added to platelet containing preparations, megapoietin or a gene encoding megapoietin can be administered to a platelet donor prior to undergoing platelet pheresis in order to increase the platelet count in the sample obtained. Further, since megakaryocytes differentiate from stem cells, megapoietin may be used for stimulating stem cells. A megapoietin protein or gene can be administered e.g., to stem cell donors to mobilize peripheral blood stem cells (pbscs) which may be obtained by leukopheresis and used instead of bone marrow as a source of stem cells (pbscs) for transplantation into a patient in need (e.g. a cancer patient).

A megapoietin protein can also be added to a "stem cell bioreactor" (i.e., stem cells cultured in vitro) to stimulate stem cell growth and replication and/or to stimulate platelet production from megakaryocytes. A preferred method for culturing stem cells is described in International Patent Application Publication No. WO 93/12805, entitled "Methods for Regulatory Lineages of Human Hematopoietic Cells".

In addition to stimulating platelet production from megakaryocytes, megapoietin also specifically binds with high affinity to a receptor located on platelet membranes. Upon binding to the platelet receptor, megapoietin is removed from the blood stream. In a normal subject, the removal of megapoietin by platelets constitutes a feedback inhibition loop maintaining a fairly constant level of platelets.

Based on the megapoietin receptor, one skilled in the art can generate monoclonal or polyclonal antibodies to the receptor. Further, one can identify megapoietin antagonists or small molecules capable of blocking the normal binding of megapoietin to the receptor. These antibodies, megapoietin antagonists or small molecules can be investigated using a "rational drug design" to formulate pharmaceutical compositions (e.g. upon admixture with appropriate carriers and excipients) and administered to thrombocythemic or high function platelet disorder patients to block the feedback inhibition triggered by the binding of endogenous megapoietin to platelet receptors. Based on preliminary experiments, low doses of vincristine and non-toxic vincristine analogues have been shown to block the binding of megapoietin to the megapoietin receptor.

Further megapoietin's platelet binding activity provides a utility for selectively targetting therapeutic or diagnostic agents to platelet containing arterial thrombi (which are involved in conditions such as myocardial infarction and stroke) in preference to venous thrombi (e.g. pulmonary emboli and deep vein thrombosis), which do not contain many platelets, if any, are normally present and in fact are necessary to prevent the escape or blood cells and fluids from an individual's vascular system. A composition of megapoietin or a platelet binding fraction of megapoietin can be conjugated (i.e. associated covalently or ionically) to an appropriate diagnostic agent (e.g. radiolabelled for example with iodine or technecium) and administered in vivo to detect arterial thrombi. Alternatively, a composition of megapoietin or a platelet binding fraction can be conjugated to a thrombolytic agent ( e.g., tissue plasminogen activator, urokinase, streptokinase, single chain streptokinase, acyl plasminogen streptokinase complex, etc.) and formulated into an appropriate pharmaceutical composition which optionally includes appropriate exipients or pharmacological carriers. An effective amount of the composition can then be administered to a patient in need of thrombolytic therapy.

The identification of megapoietin also enables diagnostic methods for identifying thrombocytopathic subjects. For example, oligonucleotide probes comprising the megapoietin gene or useful fragments can be generated and used in a hybridization procedure performed on an appropriate body fluid obtained from a subject suspected or at risk for developing a thrombocytopathy. Alternatively, polyclonal or monoclonal antibodies to the megapoietin protein or a useful fragment can be generated using standard techniques (e.g., Kohler and Milstein, Nature 256:495–497 (1975); Olsson and Kaplan, Proc. Natl. Acad. Sci. (USA) 77:5429 (1980)). Anti-megapoietin antibodies can be used for example in an immunoassay procedure to identify a subject having or at risk of developing a platelet disorder.

The present invention is further illustrated by the following examples which should not be construed as limiting in any way. The contents of all cited references (including literature references, issued patents, published patent applications, and co-pending patent applications) cited throughout this application are hereby expressly incorporated by reference.

EXAMPLE 1

Induction of Thrombocytopenia in Rats and Identification and Characterization of Megapoietin Introduction The following example describes the development of a model of non-immune thrombocytopenia in rats by subcutaneous administration of busulfan (20 mg/kg dose and 50 mg/kg dose). It also describes assays for megapoietin activity performed on plasma taken from rats on day 0 (before thrombocytopenia was induced) and on day 13 or 14 (the platelet count nadir). The example further describes the transfusion of platelets into thrombocytopenic rats and normal rats (as a control) and the effect that the added platelets have on the rat's endogenous megapoietin levels. Finally, the example describes the effect of in vitro incubation of thrombocytopenic plasma with purified platelets.

Materials

Trisodium citrate was purchased from Mallinckrodt (Paris, Ky.). Propidium iodide, adenosine (free base), theophylline, busulfan, glutaraldehyde, polyethylene glycol (average molecular weight 400), deoxyribonuclease I (DNase, type IV) and ribonuclease A (type 1-A) were obtained from Sigma (St. Louis, MO). Neutralizing rabbit antibodies to porcine TGFβ (Lots J919 and J940) were obtained from R & D Systems (614 McKinley Place N.E., Minneapolis, Minn.). Male retired breeder (600–800 g) and young (220–250 g) Sprague-Dawley-derived (CD) rats were obtained from Charles River Breeding Laboratories, Inc.(Wilmington, Mass.). All animals were housed in single cages with free access to food and water for at least one week before use. Antiserum reacting against rat platelets (APS) was prepared in rabbits as previously described (Kuter, DJ. et. al. *Blood* 74:1952 (1989)).

Methods

Preparation of Thrombocytopenic Rats

Busulfan at a concentration of 10 mg/ml in polyethylene glycol (PEG) was prepared by making a slurry at approximately 100 mg/ml in PEG and stirred for two hours at room temperature. This suspension was then brought to the final volume in PEG and heated at 74°–80° C. with stirring for two hours to dissolve residual crystals of busulfan. Rats were anesthetized with ether and injected i.p. on Days 0 and 3 with equal amounts of a total dose of busulfan of 20 mg/kg, 30 mg/kg, 40 mg/kg or 50 mg/kg.

Blood samples for cell counts were obtained from ether-anesthetized rats by inserting a 25 gauge needle into a tail vein and collecting into the needle base approximately 20 ul of freely flowing blood. Platelet and white blood cell (WBC) counts were performed using the Unipette collection system (Becton-Dickinson, Rutherford, N.J.). Platelets and white blood cells were counted (four chambers per sample) by hemacytometer (Brecher, G. and E. Cronkite *J. Appl. Physiol.* 3:365, (1950)). Rats used in these experiments had a normal platelet count of $1.404\pm0.184 \times 10^6/mm^3$ and a normal WBC count of $11.012\pm2.784\times10^3/mm^3$ (average of 8 animals).

To obtain adequate quantities of plasma for bone marrow culture, a rat was anesthetized with ether, the abdomen was opened along the mid-abdominal line and a 21 gauge needle was inserted through the intact diaphragm into the beating heart. Nine volumes of blood were drawn with gentle mixing into syringes containing one volume of 3.8% sodium citrate in Hank's Balanced Salt Solution without calcium or magnesium (HBSS). The hemmocrit was detennined, the blood was immediately centrifuged at 3,000 g for 15 minutes at 4° C. and the platelet-poor plasma (PPP) removed. After a second centrifugation at $3,000 \times g$ for 15 minutes, the PPP was frozen at $-80°$ C. The hematocrit, WBC count and platelet count were all corrected for dilution by anticoagulant.

Bone Marrow Culture

Specimens of rat PPP-derived serum (PPPDS) were prepared from rat PPP by recalcification in glass tubes and incubation at 37° C. for two hours. Clots were removed, the specimens heated at 56° C. for ½ hour and then filtered through a 0.45 micron syringe filter (Millex-HA, Millipore Products Division, Bedford, Mass. 01730). Potential TGFβ contamination was neutralized by the addition of antibody to TGF[31 as previously described (Kuter, DJ et al. *Blood* 79:619 (1992)).

Megakaryocyte-depleted rat bone marrow was prepared by the Percoll density-gradient centrifugation and filtration method (Kuter, DJ et al. *Blood* 74:1952 (1989)). The megakaryocyte-depleted bone marrow cells were resuspended to a density of $7\times10^6/ml$ (containing no more than 100 identifiable megakaryocytes/ml) in 3 ml of Iscove's Modified Dulbecco's Medium (IMDM, GIBCO, Grand Island, N.Y.) containing penicillin (200 U/mL), streptomycin (200 ug/mL), additional glutamine (0.592 mg/mL) and (unless otherwise indicated) 15% (vol/vol) rat PPPDS. Cultures were routinely grown for 3 days at 37° C. in a 5% $CO_2$ incubator. Subsequently, cells were harvested and stained for flow cytometry with APS and propidium iodide as described previously (Kuter, DJ et al. *Blood* 74:1952 (1989)).

Each experiment was performed from a single bone marrow preparation and allowed the assay of up to 20 individual specimens under identical culture conditions. Between identical plasma specimens assayed in the same bone marrow preparation, there was routinely a coefficient of variation (C.V.) of less than 1% in the ploidy of megakaryocytes which grew. Between identical plasma specimens assayed in different bone marrow preparations there was routinely a C.V. of 5–8%. These differences reflect variations in the duration of culture and in the number of megakaryocyte precursors in the marrow (Kuter, DJ et al. *Blood* 79:619 (1992)).

Platelet Transfusion

Anticoagulated blood was obtained as described above from large, retired breeder rats. The blood was inmaediately centrifuged for 8 minutes at $500 \times g$. The supernatant platelet-rich plasma (PRP) was then carefully removed. The remaining pelleted blood cells were thrice resuspended to the original volume with HBSS and centrifuged as before. The supernatants were removed and added to the original PRP. The pooled platelet suspension was centrifuged for 15 minutes at $3,000 \times g$ at 4° C. and the platelet pellet resuspended in a small volume of HBSS. This procedure recovered 50–60% of the platelets and less than 1% of the WBC in the blood sample.

On Day 13 or 14, thrombocytopenic, busulfan-treated (20 mg/kg) rats were anesthetized with ether and a 25 gauge × ⅜ inch needle attached to 3 inch tubing (Deseret Co., Sandy, Utah) was inserted into a tail vein. After demonstrating the free flow of blood, platelets were infused and the tubing rinsed with a small volume of sterile, normal saline. Animals were closely observed for one hour and none demonstrated any complications after transfusion. The platelet count obtained one hour after infusion showed that over 90% of the infused platelets were circulating.

In Vitro Incubation of Platelets with Thrombocytopenic Plasma

Pooled PRP was prepared as described above and the platelet content determined by hemacytometer. A volume of PRP that contained the same number of platelets as found in 2 ml of PRP from a normal rat was centrifuged at $3,000 \times g$ for 15 minutes and the pellet resuspended in 2 ml of thrornbocytopenic PPP. After incubation for 1 h at room temperature (RT) or 4° C. with occasional stirring, the platelets were removed by centrifuging twice at $3,000 \times g$ for 15 minutes. The supernatant PPP was then clotted as described above and assayed in bone marrow culture.

Glutaraldehyde-fixed platelets were prepared by the dropwise addition of glutaraldehyde (25% aqueous solution) to the pooled PRP to a final concentration of 2%. After one hour incubation at room temperature, platelets were collected by centrifugation at $3,000 \times g$ and resuspended in HBSS. Platelets were subsequently washed two more times in this manner to remove residual fixative and stored as a concentrated suspension in HBSS at 4° C. Incubation of these fixed platelets with thrombocytopenic plasma was done at room temperature as described above.

Flow Cytometry

Flow cytometry was performed as previously described (Kuter, DJ et al. *Blood* 79:619 (1992)) on a machine designed by H. Shapiro (Shapiro, HM: Practical Flow Cytometry. New York, N.Y., Liss (1985)) and built by Y. G. Caine. A coefficient of variation of the 2N peak was maintained at 1.97 to 2.94% by careful alignment of the optical system. Cells were routinely run at 800 to 1200 cells/s and 1000 megakaryocytes were analyzed.

Data Analysis

Data from the flow cytometer were stored and analyzed on an Atari 130 XE computer (Sunnyvale, Calif.). The total number of nucleated cells and the total number of megakaryocytes in each assay were quantitated as previously described (Kuter DJ et al. *Blood* 79:619 (1992)). Boundaries between each ploidy class were assigned from the DNA histogram and the number of megakaryocytes in each ploidy group (4N–32N) was counted. The number of megakaryocytes in each ploidy class was then expressed as a percentage of the total number of megakaryocytes $\geq$ 4N. The geometric mean ploidy for each distribution 4N–32N (Mean Ploidy 4N–32N) was determined as described by Arriaga (Arriaga, M et al. *Blood* 69:486 (1987)). The rise in megakaryocyte number in culture is less pronounced than the increase in megakaryocyte ploidy and is usually seen only at higher levels of megapoietin (MP). In addition, the changes in megakaryocyte number are measured by flow cytometer with less sensitivity than the changes in megakaryocyte ploidy. Because of these differences in assay sensitivity MP was routinely quantitated by measuring only its effect on ploidy. MP was therefore expressed as the Mean Ploidy 4N–32N for each sample tested.

Except for ploidy distributions, statistical analysis of differences was performed with Student's t test (Swinscow, TDV: Statistics at Square One. Bath, UK, Mendip (1979)). Differences between ploidy distributions were tested for using the Mann-Whitney U test (Wynne JD: Learning Statistics. New York, N.Y., MacMillan, (1982)) as previously described (Kuter, DJ et al. *Blood* 75:74 (1990)).

Results

Low Dose Busulfan (20 mg/kg) Produced Prolonged Thrombocytopenia but not Leukopenia in the Rat Rats injected with 50 mg/kg of busulfan developed profound thrombocytopenia with a half-maximal decline on Day 6.5 and a nadir on Day 10. Unfortunately, the WBC count also declined to a nadir of $0.371 \pm 0.262 \times 10^3/mm^3$ by Day 11. In addition, the rats stopped eating, lost weight, had persistent melenotic diarrhea, developed poor coat texture, became anemic and were all dead by Day 12. At lower busulfan doses of 40 mg/kg and 30 mg/kg, the same effects occurred except that the half-maximal platelet decline was delayed to Day 7.5 and the platelet nadir was delayed to Day 11 for both doses. However, at a dose of 20 mg/kg, thrombocytopenia was just as profound as at the higher doses of busulfan but was accompanied by few other major problems. Rats treated with the 20 mg/kg dose of busulfan had a half-maximal decline in platelet count on Day 9.5 and a nadir on Day 13.5. This platelet nadir of $0.016 \pm 0.08 \times 10^6/mm^3$ persisted for at least 6 days before gradually rising. Some rats remained severely thrombocytopenic (platelet counts<50,000/mm$^3$) for 6 months but the majority of rats returned to a normal platelet count over three weeks.

At a busulfan dose of 20 mg/kg, there was no statistically significant decline in the WBC count. Animals treated with 20 mg/kg busulfan had a WBC count on Day 14 that was the same as uninjected control animals.

At the 20 mg/kg busulfan dose the rats appeared healthy with normal feeding, stool production and coat texture. There was no overt or occult bleeding detected in any animal. However when compared to uninjected controls, they gained only half as much weight. In addition, like those rats treated with the 50 mg/kg busulfan dose, they also developed a moderate anemia.

Plasma Obtained From Thrombocytopenic, Busulfan-Treated Rats Contained MP

Plasma obtained from rats prior to busulfan injection (20 mg/kg), when the animals were not yet thrombocytopenic, had no increased MP. However plasma obtained at the platelet nadir on Day 13 or 14 stimulated visible megakaryocyte growth in culture. When quantitated by flow cytometry, plasma from thrombocytopenic, busulfan-treated (20 mg/kg) animals had no effect on the total number of cells which grew in culture but stimulated the number of megakaryocytes which grew compared with plasma from uninjected rats with normal platelet counts. In addition, plasma from thrombocytopenic, busulfan-treated rats caused a marked increase in megakaryocyte ploidy with a shift in the modal ploidy class from 8N to 16N and a rise in the mean ploidy (MP) from $8.656 \pm 0.381$ to $13.622 \pm 1.270$. In contrast, the plasma from rats treated with higher doses of busulfan (e.g., 50 mg/kg dose) demonstrated comparable ploidy changes, but no increase in the number of megakaryocytes. These plasmas also produced a 50% increase in the total number of cells per culture that was entirely the consequence of a rise in maturing myeloid cells (Kuter DJ et al. *Blood* 74:1952 (1989)), probably related to the increased levels of G-CSF found in the serum of these neutropenic animals.

Platelet Transfusion Reduced the Levels of MP in Thrombocytopenic Rats

To demonstrate that the rise in MP was directly related to the absence of platelets and not to some other effect of the busulfan treatment, platelets were transfused into thrombocytopenic rats and the animals sacrificed 24 hours later. Transfusion of platelets into thrombocytopenic rats raised the platelet count from $0.017 \pm 0.009 \times 10^6/mm^3$ to $2.008 \pm 0.214 \times 10^6/mm^3$ one hour after transfusion. Twenty-four hours later the animals still maintained platelet counts above normal at $1.535 \pm 0.143 \times 10^6/mm^3$. In all other aspects, the transfused and untransfused thrombocytopenic rats were identical but both groups of busulfan treated rats differed from normal rats in their weight and hematocrit as described above.

When compared to plasma from normal rats, plasma from thrombocytopenic rats which had not been transfused had no effect on the total number of cells which grew in bone marrow culture but increased the total number of megakaryocytes by 16%. In addition, the modal ploidy class was shifted from 8N to 16N and the mean ploidy increased from $8.757 \pm 0.135$ to $10.801 \pm 0.262$. However, the transfusion of platelets into thrombocytopenic animals reduced these elevated MP levels to normal. Plasma from thrombocytopenic animals which had been transfused with platelets showed no difference from normal plasma in either the number or ploidy distribution of megakaryocytes which grew in culture.

In Vitro Incubation of Thrombocytopenic Plasma with Purified Platelets Completely Removed MP To determine whether platelets might directly be responsible for the reduction of MP noted after platelet transfusion in vivo, purified rat platelets were added to thrombocytopenic plasma in vitro in amounts equal to that found in an equivalent volume of normal, platelet-rich plasma and the effect on the level of MP quantitated. As expected, in the absence of platelets, thrombocytopenic plasma promoted a maximal (defined to be 100%) rise in MP compared with that in plasma from normal animals (defined to be 0%). Upon incubation with platelets at room temperature, all of the MP was eliminated. Incubation with platelets at 4° C. eliminated two-thirds of the activity, similar to that seen upon incubation at room temperature with an equal number of glutaraldehyde-fixed rat platelets. Addition of platelets to normal plasma showed no significant effect. When these experiments were repeated in the presence of antibody to TGF-β, identical results were obtained.

SUMMARY

Fourteen days following the administration of 20 mg/kg busulfan, the platelet count reached a nadir of less than 2% of the initial value and remained at this level for no less than 6 days. The hematocrit dropped by 20% over this time, but there was no significant decrease in the white blood cell count. The animals remained healthy and without spontaneous bleeding. Thrombocytopenic plasma, but not normal plasma, from these animals was found to stimulate the number and ploidy of megakaryocytes which grew in a bone marrow culture system. To demonstrate that the elevated levels of megapoietin were a response to the thrombocytopenia and not to the means by which the thrombocytopenia was generated, platelets were infused into thrombocytopenic animals and the levels of megapoietin were reduced to normal. Finally, platelets were found to bind to and remove megapoietin from thrombocytopenic plasma in vitro. These results provide evidence that megapoietin is a humoral mediator of megakaryocytopoiesis.

EXAMPLE 2

Induction of Thrombocytopenia in Rabbits; and Characterization of Megapoietin

Introduction

The following example describes the development of a model of non-immune thrombocytopenia in rabbits by subcutaneous administration of busulfan (50 mg/kg). It also describes assays for megapoietin activity performed on plasma taken from rabbits on day 0 (before thrombocytopenia was induced) and on days 13 or 14 (the platelet count nadir). The example further describes the transfusion of platelets into thrombocytopenic rabbits and normal rabbits (as a control) and the effect that platelets have on the megapoietin level of rabbits. Finally, the example describes the effect of in vitro incubation of thrombocytopenic plasma with purified platelets.

Materials

Trisodium citrate was purchased from Mallinckrodt (Paris, Ky.). Propidium iodide, adenosine (free base), theophylline, busulfan, polyethylene glycol (average molecular weight 400), deoxyribonuclease I (DNase, type IV) and ribonuclease A (type 1-A) were obtained from Sigma (St. Louis, Mo.). Neutralizing rabbit antibodies to porcine TGFβ (Lots J919 and J940) were obtained from R & D Systems (614 McKinley Place N.E., Minneapolis, Minn.). Male retired breeder (600–800 g) Sprague-Dawley-derived (CD) rats were obtained from Charles River Breeding Laboratories, Inc. (Wilmington, Mass.) and New Zealand White rabbits (3 kg) were from Hazleton Research Products, Inc. (310 Swamp Bridge Road, Denver Pa.). All animals were housed in single cages with free access to food and water for at least one week before use. Antiserum reacting against rat platelets (APS) was prepared in rabbits as previously described (Kuter, DJ et al. Blood 74:1952 (1989)).

Methods

Preparation of Thrombocytopenic Rabbits

Busulfan at a concentration of 10 mg/ml in polyethylene glycol (PEG) was prepared by making a slurry at approximately 100 mg/ml in PEG and stirred for two hours at room temperature. This suspension was then brought to the final volume in PEG and heated at 74°–80° C. with stirring for two hours to dissolve residual crystals of busulfan. Rabbits were restrained, one ear swabbed with 95% ethanol and the lateral vein cannulated with a 23 gauge scalp vein infusion set (Infusion Set, 23G × ¾ inch, 12 inch tubing, Deseret Medical Inc., Sandy, Utah.). Between 0.75 and 1.25 ml of sodium pentobarbital (65 mg/ml, Anthony Products Co., Arcadia, Calif.) were infused over one to two minutes to produce anesthesia. After preparing the injection site by shaving off all the hair and scrubbing the site with 95% ethanol, busulfan (25 mg/kg per injection) was then administered by a single, deep subcutaneous injection into alternate sides of the lower abdomen on Days 0 and 3. Animals were observed closely for one hour before being returned to their cages and were monitored daily for the next 15 to 100 days.

At intervals, one to five milliliters of blood were removed aseptically from the lateral ear vein with a 23 gauge scalp vein infusion set for cell counts and for addition to bone marrow culture. Nine volumes of blood were drawn with gentle mixing into syringes containing one volume of 3.8% sodium citrate. An aliquot of anticoagulated blood was then drawn into the Unipette collection system (Becton-Dickinson, Rutherford, N.J.) for platelet and white blood cell (WBC) count determinations using the hemacytometer (four chambers per sample) (Brecher, G. and E. Cronkite J. Appl. Physiol. 3:365 (1950)). A second aliquot was drawn into a microhematocrit capillary tube (Fisher Scientific Co., Pittsburgh, Pa.) and the hematocrit determined after centrifugation. The hematocrit, WBC count and platelet count were all corrected for dilution by the anticoagulant. The remaining blood was immediately centrifuged. at 3,000 × g for 15 minutes at 4° C. and the platelet-poor plasma (PPP) removed. After a second centrifugation at 3,000 × g for 15 minutes, the PPP was frozen at 80° C.

Bone Marrow Culture

Specimens of rabbit PPP-derived serum (PPPDS) were prepared from rabbit PPP by recalcification in glass tubes and incubation at 37° C. for two hours. Clots were removed, the specimens heated at 56° C. for ½ hour and then filtered through a 0.45 micron syringe filter (Millex-HA, Millipore Products Division, Bedford, Mass.). Potential TGFβ contamination was neutralized by the addition of antibody to TGF β1 as previously described (Kuter, DJ et al. Blood 79:619 (1992)).

Megakaryocyte-depleted rat bone marrow was prepared by the Percoll density-gradient centrifugation and filtration method (Kuter, DJ et al. Blood 74:1952 (1989)). The megakaryocyte-depleted bone marrow cells were resuspended to a density of $7 \times 10^6$/mL (containing no more than 100 identifiable megakaryocytes/mL) in 3 mL of Iscove's Modified Dulbecco's Medium (IMDM, GIBCO, Grand Island, N.Y.) containing penicillin (200 U/mL), streptomycin (200 ug/mL), additional glutamine (0.592 mg/mL) and (unless otherwise indicated) 15% (vol/vol) rabbit PPPDS. Cultures were routinely grown for 3 days at 37° C. in a 5% $CO_2$ incubator. Subsequently, cells were harvested and stained for flow cytometry with APS and propidium iodide as described previously (Kuter, DJ et. al. Blood 79:619 (1992)).

Each experiment was performed from a single bone marrow preparation, which allowed up to 20 individual specimens to be assayed under identical culture conditions. Between identical plasma specimens assayed in the same bone marrow preparation, there was routinely a coefficient of variation (C.V.) of less than 1% in the ploidy of megakaryocytes which grew. Between identical plasma specimens assayed in different bone marrow preparations, there was routinely a C.V. of 5–8%. These differences reflect variations in the duration of culture and in the number of megakaryocyte precursors in the marrow (Kuter, DJ et al. Blood 79:619 (1992)).

Platelet Transfusion

Blood was obtained from donor rabbits that were anesthetized with pentobarbital and then exsanguinated by direct cardiac puncture. Nine parts of blood were collected into one part of disodium EDTA (1.66% in water) and the anticoagulated blood was immediately centrifuged for 8 minutes at 500 × g. The supernatant platelet-rich plasma (PRP) was then carefully removed. The remaining pelleted blood cells were twice resuspended to the original volume with Hanks' Balanced Salt Solution without calcium or magnesium (HBSS) and centrifuged as before. The supernatants were removed and added to the original PRP. The pooled platelet suspension was centrifuged for 15 minutes at 3,000 × g at 4° C. and the platelet pellet (containing $42–47 \times 10^9$ platelets) resuspended in 4 ml of HBSS. From 250 ml of anticoagulated blood, about 65% of the total platelets and less than 1% of the WBC were recovered by this method.

On Day 14 or 15, the lateral ear vein of thrombocytopenic, busulfan-treated rabbits was cannulated with a 23 gauge scalp vein infusion set. After demonstrating the free flow of blood, platelets were infused over three to five minutes and the tubing rinsed with a small volume of sterile normal saline. Animals were closely observed for one hour and none demonstrated any complications after transfusion. The platelet count obtained three hours after infusion showed that over 90% of the infused platelets were circulating.

In Vitro Incubation of Platelets with Thrombocytopenic Plasma

PRP was prepared from a normal donor rabbit as described above and the platelet content determined by hemacytometer. A volume of PRP that contained the same number of platelets as found in 2 ml of whole blood from a normal rabbit was centrifuged at 3,000 × g for 15 minutes and the pellet resuspended in 1.25 ml (the amount of PPP in 2 ml of whole blood) of thrombocytopenic rabbit PPP. After incubation for 1 hour at 4° C. or at 20° C. with occasional stirring, the platelets were removed by centrifuging twice at 3,000 × g for 15 minutes. The supernatant PPP was then clotted as described above and assayed in bone marrow culture.

Flow Cytometry

Flow cytometry was performed as previously described (Kuter, DJ et al. *Blood* 79:619 (1992)) on a machine designed by H. Shapiro (Shapiro, HM Practical Flow Cytometry New York, N.Y. Liss 1985) and built by Y. G. Caine. A coefficient of variation of the 2N peak was maintained at 1.97 to 2.94% by careful alignment of the optical system. Cells were routinely run at 800 to 1200 cells/sec and 1000 megakaryocytes were analyzed.

Data Analysis

Data from the flow cytometer were stored and analyzed on an Atari 130 XE computer (Sunnyvale, Calif.). The total number of nucleated cells and the total number of megakaryocytes in each assay were quantitated as previously described (Kuter, DJ et al. *Blood* 79:619 (1992)). Boundaries between each ploidy class were assigned from the DNA histogram and the number of megakaryocytes in each ploidy group (4N–32N) was counted and then expressed as a percentage of the total number of megakaryocytes≧4N. The geometric mean ploidy for each distribution 4N–32N (Mean Ploidy) was determined as described by Arriaga (Arriaga et al. *Blood* 69:486 (1987)). The rise in megakaryocyte number in culture is usually less pronounced than the increase in megakaryocyte ploidy and is seen only at higher levels of megapoietin. In addition, the changes in megakaryocyte number are measured by flow cytometry with less sensitivity and less precision than the changes in megakaryocyte ploidy. Because of these differences between using change in the number of megakaryocytes versus change in the ploidy of megakaryocytes to quantitate megapoietin, megapoietin was routinely measured for each sample by assessing its effect only on ploidy (as expressed by the Mean Ploidy).

Except for ploidy distributions, statistical analysis of differences was performed with Student's t test (Swinscow, TDV Statistics at Square One Bath U.K. Mendip 1979)). Differences between ploidy distributions were tested for using the Mann-Whitney U test (Wynne JD: Learning Statistics. New York, N.Y., MacMillan, 1982) as previously described (Kuter, DJ et al. *Blood* 79:619 (1992)). The coefficient of determination, $r^2$, was determined by simple linear regression analysis (Zar JH: Biostatistical Analysis. Englewood Cliffs NJ Prentice-Hall, 1974).

Results

Busulfan Treatment Produced Severe Thrombocytopenia But Only Modest Leukopenia in Rabbits Following the injection of a total of 50 mg/kg of busulfan in two equal doses on Days 0 and 3, the decline in platelet count followed a very reproducible pattern. There was no decline from the average pre-treatment platelet count of 456250±78646/µl up to Day 6 but then the count dropped rapidly over the next week down to a nadir on Day 14±1 of 11696±10730/µl, an average decline to 2.6% of the pretreatment value. The platelet count usually remained below 10% of the pre-treatment value from Day 12 to Day 19 and then returned to normal over the next two to three weeks without a rebound thrombocytosis.

In those animals in whom phlebotomy was minimal, the hematocrit declined gradually over two weeks from an average of 37.4±2.5 to a nadir on Day 13±2 of 30.9±1.9, an average drop of 17%.

The response of the WBC count was more variable. In 13 of the 17 animals analyzed, the average pre-treatment WBC count of 8826±2052/µl fell gradually over 2 weeks to a nadir on Day 13±1 of 5849±1889/µL, an average drop of 34%. Four animals experienced severe leukopenia (WBC count<2000/µl) which occurred on Day 13 and necessitated their sacrifice (a pre-study parameter established to insure optimal animal care). All four were found to have woody edema and necrosis at the injection sites which were related to the inadvertent intradermal injection of the busulfan. However, in 52 subsequent animals that were meticulously injected subcutaneously rather than intradermally, this problem has not recurred.

Except for this complication, all animals appeared healthy with no weight loss, decline in appetite or stool production, or change in coat texture. There was no overt or occult bleeding detected in any of the animals. Following resolution of the thrombocytopenia, all the peripheral blood cell counts returned to normal. Several animals have been followed for over three years and none of the animals has exhibited any evidence of a hematological abnormality.

Plasma From Thrombocytopenic, Busulfan-Treated Rabbits Stimulated the Number and Ploidy of Megakaryocytes Which Grew in Bone Marrow Culture The effect in bone marrow culture of thrombocytopenic plasma obtained at the platelet nadir to that of plasma obtained prior to treatment was compared for six rabbits. For all animals, plasma obtained at the platelet nadir markedly stimulated the number, size and ploidy of megakaryocytes which grew in bone marrow culture. This effect was visually apparent by inspection of the cultures using phase contrast microscopy and was readily quantitated by flow cytometry. All thrombocytopenic plasmas stimulated an increase in the total number of megakaryocytes per culture from 9312±1679 to 14063±3178, an average rise to 150±17% of the pretreatment values. Likewise, all thrombocytopenic plasmas stimulated a shift in the modal megakaryocyte ploidy class from 8N to 16N and an average rise in the Mean Ploidy from 9.1±0.3 to 14.6±1.3, an increase to 158±20% of the pretreatment values.

Urine from several thrombocytopenic rabbits was collected, the protein concentrated by 80% ammonium sulfate precipitation and then dialyzed against culture medium. Unlike simultaneous serum specimens, none of the urine specimens showed any stimulatory activity when added to bone marrow culture.

The Extent of Stimulation on Megakaryocytes is Inversely Proportional to Platelet Count To determine whether the extent of the stimulatory effect of thrombocytopenic plasma (megapoietin concentration) was related to the degree of thrombocytopenia of the donor rabbit, five rabbits were treated with busulfan and samples taken at variable intervals from Day 0 to Day 100. The extent of stimulation of both the number and ploidy of megakaryocytes for all the animals was found to be inversely proportional to the platelet count on the day the plasma sample was obtained. The stimulatory activity first appeared on Day 8±2 at a time when the platelet count was usually about 50% of normal and the level of stimulatory activity peaked during the platelet nadir. With a rise in the platelet count toward normal, the stimulatory effect rapidly declined. At a platelet count of about 50% of normal, the stimulatory effect was again near to the baseline (Day 0) value. Although summarized best by the changes in Mean Ploidy, the extent of stimulation by the thrombocytopenic plasma was also readily apparent by the changes seen in each individual ploidy class and by the change in the number of megakaryocytes which grew in culture (Table 1).

interruption of a feedback loop which stimulates megapoietin production or it may be due to the effect of platelets directly removing the circulating megapoietin. To see if the latter mechanism was a consideration, rabbit platelets were added back to thrombocytopenic rabbit plasma in vitro in an amount identical to that which would be found in platelet-rich plasma from a non-thrombocytopenic rabbit. When incubated at 4° C., platelets removed 42% of the stimulatory effect on megakaryocyte ploidy. However, at 20° C., platelets removed 95% of the stimulatory effect on megakaryocyte ploidy. Identical results were obtained in the presence of neutralizing antibody to TGF-β1. When pre-treatment (normal) plasma was incubated with rabbit platelets in parallel experiments, there was no effect of the platelet

TABLE 1

| DAY | PLATELET COUNT (per μl) | TOTAL NUMBER OF MEGAKARYOCYTES PER CULTURE | 4N (%) | 8N (%) | 16N (%) | 32N (%) | MEAN PLOIDY |
|---|---|---|---|---|---|---|---|
| 0 | 461111 | 8497 ± 117 | 17.2 ± 0.2 | 46.0 ± 0.4 | 32.4 ± 0.5 | 4.4 ± 0.7 | 9.5 ± 0.1 |
| 6 | 443056 | 8282 | 18.3 | 40.0 | 35.8 | 5.9 | 9.8 |
| 8 | 146292 | 10230 | 11.0 | 35.1 | 43.2 | 10.7 | 11.6 |
| 12 | 56667 | 9554 | 10.2 | 18.8 | 45.8 | 25.1 | 14.5 |
| 16 | 4444 | 12151 | 11.2 | 14.9 | 46.8 | 27.2 | 14.9 |
| 18 | 20500 | 13139 | 8.1 | 22.1 | 47.6 | 22.2 | 14.3 |
| 22 | 206667 | 9451 | 10.3 | 40.2 | 41.8 | 7.7 | 11.1 |
| 24 | 287500 | 8800 | 13.9 | 45.8 | 34.2 | 6.1 | 10.0 |
| 26 | 361111 | 9281 | 15.7 | 43.5 | 35.3 | 5.5 | 9.9 |
| 30 | 338750 | 8400 | 13.3 | 53.0 | 29.7 | 4.0 | 9.5 |

Platelet Transfusion Reduced the Level of Megapoietin in Thrombocytopenic Busulfan-Treated Rabbits To determine whether the elevated level of megapoietin found in the circulation of thrombocytopenic, busulfan-treated rabbits was really due to the low platelet count and not due to the means by which the platelet count had been lowered, platelets were transfused into thrombocytopenic rabbits as they approached their platelet nadir and the effect on the circulating level of megapoietin was measured. Three hours after increasing the platelet count from 6.2% to 41% of normal, the megapoietin level dropped into the normal range (mean ploidy decreased from 11.3±0.2 to 8.9±0.2, an 89±8% decline). As the platelet count subsequently decreased after transfusion, the level of megapoietin again rose to maximum, only to fall again as the rabbit's own platelet production recovered.

Since platelet transfusion did not restore the platelet count entirely to its pre-treatment level, the decline in the level of megapoietin was only partial but was identical to that which would have been predicted for this degree of thrombocytopenia. Therefore if the pre-transfusion and post-transfusion megapoietin levels represent steady-state values, the data suggests that megapoietin has a circulating half-life under 45 minutes.

This experiment has been repeated using a second animal with similar results. On Day 14, a second rabbit received a platelet transfusion of 47×10⁹ rabbit platelets which raised the platelet count from 3% of the pre-treatment value to 37%. Plasma taken 3 hours after the transfusion lost 81±8% of its stimulatory effect on megakaryocyte ploidy when compared with pre-transfusion (thrombocytopenic) and pre-treatment (normal) plasmas.

Rabbit Platelets Removed Megapoietin From Thrombocytopenic Rabbit Plasma in Vitro The reduction in megapoietin levels seen following platelet transfusion in vivo may be an indirect effect due to the addition on the ploidy of megakaryocytes which grew in culture.

The Megapoietin in Thrombocytopenic, Busulfan-Treated Rabbit Plasma is Due to the Presence of a Positive Effector, Not the Absence of an Inhibitor To determine whether the stimulatory effect of thrombocytopenic plasma was due to the appearance of a positive effector in plasma and not the loss of an inhibitor, the effects of pre-treatment (normal) plasma and thrombocytopenic plasma were compared at different concentrations and after making a 1:1 mix. At concentrations of both 15% and 30%, pre-treatment plasma produced the same small number of low ploidy megakaryocytes in culture in contrast to the much larger number of high ploidy megakaryocytes produced by thrombocytopenic plasma. The 1:1 mix (30% total plasma concentration) still produced the increased number and ploidy of megakaryocytes characteristic of the thrombocytopenic plasma.

Thrombocytopenic Plasma Stimulated the Number and Ploidy of Megakaryocytes in Culture in a Dose-Dependent Manner The results of the 1:1 mix suggested an assay system for megapoietin might be developed by adding thrombocytopenic plasma (or partially-purified fractions) to a rat bone marrow culture grown in plasma from a normal rabbit and then assessing the effect on the number and ploidy of megakaryocytes which grew. To determine the feasibility of such an assay system, increasing mounts of thrombocytopenic rabbit plasma were added to basal cultures grown in 15% normal rabbit plasma and the effect on the number and ploidy of megakaryocytes which grew was determined. Between concentrations of 0 and 15% thrombocytopenic plasma, there was found to be an almost linear increase in the Mean Ploidy and in the number of megakaryocytes which grew. Each individual ploidy class also showed proportional changes as more thrombocytopenic plasma was added. With stimulation being seen at thrombocytopenic plasma concentrations as low as 1.67%, changes in megakaryocyte ploidy were a more sensitive indicator of megapoietin activity than changes in the number of megakaryocytes, which increased only after the addition of 5% thrombocytopenic plasma. Addition of up to 15% pretreatment (normal) plasma to these basal cultures was without any effect.

Summary.

Fourteen days following subcutaneous administration of 50 mg/kg busulfan to six rabbits, the platelet count dropped to about 2.6% of their pretreatment levels with minimal effect on the hematocrit and white blood cell count. The animals remained healthy and without spontaneous bleeding. Thrombocytopenic plasma from these animals but not pretreatment plasma was found to stimulate the number and ploidy of megakaryocytes which grew in a bone marrow culture system. Levels of megapoietin in the circulation were then measured over the entire time course following administration of busulfan. As the platelet mass declined, levels of megapoietin rose inversely and proportionally and peaked during the platelet nadir. With recovery of the platelet mass toward normal, megapoietin levels fell accordingly. When platelets were transfused into thrombocytopenic rabbits near the time of their platelet count nadir, the elevated levels of megapoietin fell. In addition, platelets were found to remove megapoietin from thrombocytopenic plasma in vitro. These results provide evidence that megapoietin is a humoral mediator of megakaryocytopoiesis.

EXAMPLE 3

Induction of Thrombocytopenia in 106 Sheep; and Purification of Megapoietin

Introduction

The following example describes the development of a model of non-immune thrombocytopenia in 106 sheep by subcutaneous administration of busulfan (900 mgs/m$^2$ of body surface area).

Materials and Methods

Figure 2:
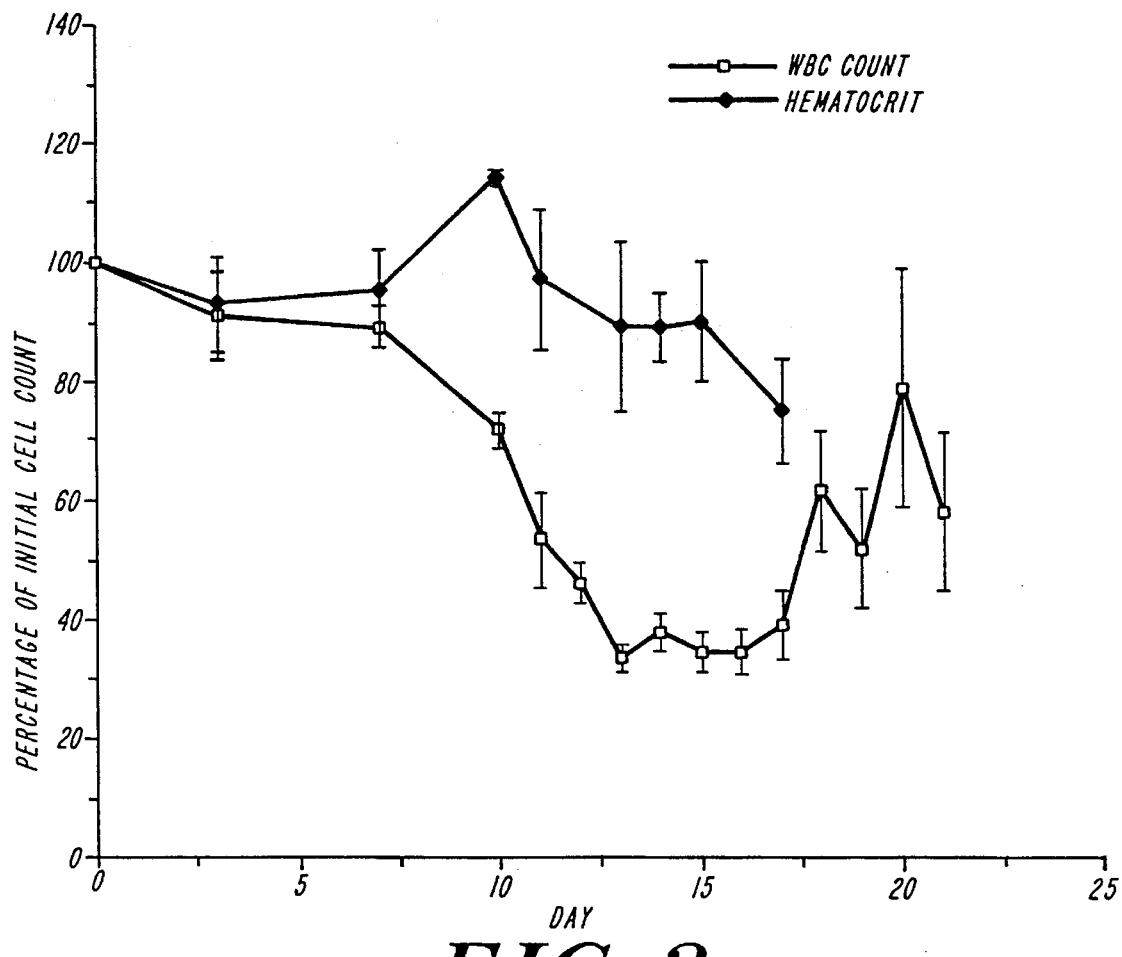
FIG. 2 is a graph plotting the average white blood cell (wbc) count and hematocrit count over the same 22 day period for the same 106 sheep injected subcutaneously with 900 mg. of busulfan/$m^2$ of body surface area on days 0 and 3, for which the corresponding platelet count is shown in FIG. 1.

After considerable dosage experimentation in sheep, the dose of 900 mg/m$^2$ body surface area was found to provide optimal thrombocytopenia in sheep without detrimental side-effects. This total dose of busulfan (10 mg/ml in polyethylene glycol (400 MW)) was injected into 106 sheep in two equal amounts on days 0 and 3. Baseline (day 0) sheep values were: WBC=5919±1.179 mm$^3$, platelets=508,000±86,000 per mm3; and hematocrit=46.8±5.7. The change in these hematological values over twenty two days are shown in FIGS. 1 and 2. Nadir of platelet counts occurred on average on about days 16–17 and nadir of white blood cell (WBC) counts on days 13–16.

Serial blood samples were taken from 6 sheep over the entire course following the busulfan injection and the flow cytometer assay described above was used to document the appearance in the circulation of MP. The data for 6 animals pre-busulfan treatment and at their platelet count nadir is presented in Table 2 below.

TABLE 2

| sheep | # platelets | (%) | # megakaryocytes | (%) | 4N | 8N | 16N | 32N | 64N | MP | (%) |
|---|---|---|---|---|---|---|---|---|---|---|---|
| PRETREATMENT | | | | | | | | | | | |
| 509 | 505 | 100 | 2401 | 100 | 36.1 | 38.12 | 23.54 | 2.24 | 0 | 7.56 | 100 |
| 508 | 379 | 100 | 852 | 100 | 7.95 | 46.58 | 41.92 | 3.56 | 0.27 | 10.76 | 100 |
| 537 | 323 | 100 | 2412 | 100 | 14.69 | 47.39 | 34.6 | 3.32 | 0 | 9.62 | 100 |
| 539 | 413 | 100 | 5001 | 100 | 30.95 | 52.63 | 15.66 | 0.75 | 0 | 7.27 | 100 |
| 583 | 464 | 100 | 3447 | 100 | 18.05 | 44.4 | 33.39 | 4.15 | 0.15 | 9.49 | 100 |
| 555 | 827 | 100 | 5107 | 100 | 16.46 | 34.96 | 39.43 | 9.15 | 1.02 | 11.11 | 100 |
| AVG | 485 | 100 | 3203 | 100 | 20.7 | 44.01 | 31.42 | 3.86 | 0.48 | 9.3 | 100 |
| SD | 179 | | 1656 | | 10.64 | 6.47 | 9.99 | 2.85 | 0.47 | 1.59 | |
| THROMBOCYTOPENIC | | | | | | | | | | | |
| 509 | 126 | 25 | 3034 | 126 | 8.19 | 30.38 | 44.03 | 17.4 | 0 | 13.06 | 173 |
| 508 | 61 | 16 | 2893 | 340 | 4.65 | 19.03 | 54.2 | 21.5 | 0.66 | 15.4 | 143 |
| 537 | 172 | 53 | 7380 | 306 | 7.72 | 21.14 | 58.67 | 12.5 | 0 | 13.54 | 141 |
| 539 | 33 | 8 | 6101 | 122 | 8.28 | 35.86 | 48.28 | 7.57 | 0 | 11.72 | 161 |
| 583 | 61 | 13 | 6541 | 190 | 26.23 | 17.01 | 21.93 | 30.7 | 4.98 | 13.44 | 142 |
| 555 | 199 | 24 | 6630 | 130 | 10.26 | 17.95 | 34.71 | 32 | 5.13 | 16.42 | 148 |
| AVG | 109 | 23 | 5430 | 202 | 10.89 | 23.56 | 43.64 | 20.3 | 3.59 | 13.93 | 151 |
| SD | 67 | 16 | 1955 | 97 | 7.73 | 7.73 | 13.49 | 9.78 | 2.54 | 1.7 | 13 |

As with the thrombocytopenic rat and rabbit plasmas, sheep thrombocytopenic plasma was found to stimulate an increase in the number and size of megakaryocytes which was visually apparent. In addition, the stimulatory effect of sheep thrombocytopenic plasma (i.e., megapoietin) was due to the presence of a positive effector, not the absence of an inhibitor. This was demonstrated in the following 1:1 mixing experiment in which normal (pre-treatment) plasma and thrombocytopenic plasmas were assayed at both 15 and 30% and compared with the effect of a 1:1 mix of normal and thrombocytopenic plasmas (15% of each). The data presented in Table 3 shows that the 1:1 mix stimulated ploidization and an increase in the number of megakaryocytes and was identical to the thrombocytopenic samples (data are given ±SD).

TABLE 3

| Plasma Source | #MKs | 4N (%) | 8N (%) | 16N (%) | 32N (%) | 64N (%) | Mean ploidy |
|---|---|---|---|---|---|---|---|
| NML-15% | 6551 | 15.45 | 46.6 | 32.82 | 4.75 | 0.48 | 9.75 |
| | 238 | 0.23 | 1.5 | 0.2 | 0.5 | 0.46 | 0.14 |
| NML-30% | 4633 | 12.95 | 43.52 | 37.01 | 5.9 | 0.64 | 10.4 |

TABLE 3-continued

| Plasma Source | #MKs | 4N (%) | 8N (%) | 16N (%) | 32N (%) | 64N (%) | Mean ploidy |
|---|---|---|---|---|---|---|---|
| | 705 | 1.92 | 0.32 | 1.86 | 0.16 | 0.11 | 0.23 |
| 1:1 MIX | 7699 | 13.52 | 19.05 | 40.55 | 24.9 | 1.98 | 14.21 |
| | 959 | 1.26 | 2.1 | 1.24 | 2.11 | 0.9 | 0.83 |
| TC-15% | 8335 | 17.14 | 17.95 | 34.65 | 28.24 | 2.02 | 14.02 |
| | 922 | 4.58 | 5.03 | 4.1 | 5.09 | 0.51 | 1.87 |
| TC-30% | 8133 | 18.66 | 18.67 | 33.03 | 27.74 | 1.91 | 13.54 |
| | 878 | 3.34 | 3.63 | 2.57 | 4.7 | 0.3 | 1.35 |

As can be ascertained from the data, there is no evidence of an inhibitor. MP is solely a stimulatory factor.

Blood was collected from 106 sheep during several days of the platelet nadir into 3.8% disodium citrate (9 parts blood to one part citrate), centrifuged at 4000 × g for 15 minutes, the plasma removed and centrifuged a second time to remove residual debris. Red blood cells were resuspended in sterile PBS and reinfused into the animal. The plasma was then stored at −20° C. It retained full activity for over 2 years.

Tissues from thrombocytopenic animals have been extracted. Lung was found to have the most activity. Heart, liver and kidneys on the other hand exhibited little or no activity. It is therefore believed that lung is the primary site of megapoietin production.

EXAMPLE 4

A Novel Serotonin Assay for Megapoietin

Introduction

This Example describes the development of a novel serotonin incorporation assay for efficiently and accurately detecting megapoietin activity.

Materials and Methods

In order to assay thousands of samples necessary to purify MP, an easier assay than the flow cytometer assay was needed. Rat bone marrow was isolated and RBCs lysed as before (Kuter, DJ et al. *Blood* 74:1942 (1989)), then mature bone marrow megakaryocytes were removed by filtration through a 17 micron mesh, and the remaining cells washed and placed into culture in IMDM containing (non-stimulatory) 15% rabbit plasma-derived serum. These conditions allow survival of the cells but little stimulation of the megakaryocytes. Upon the addition of samples containing MP, exuberant megakaryocyte growth occured. After 3 days of growth, labeled serotonin (a total of approximately 80,000 cpm) was added to each culture well, incubated for 3–6 hours (about 5 hours appears to be optimal), the cells washed and the cell pellet then counted for its content of labeled serotonin. Control experiments have shown that over 90% of the label is in megakaryocytes. Serotonin incorporation measures the mass of megakaryocytes (and is comparable to the product of the number of megakaryocytes × the mean ploidy from the flow cytometry assays).

The serotonin assay has been found to display a linear dose-response relationship over much of its range. When normal and thrombocytopenic plasma are compared, the normal plasma shows no stimulation while thrombocytopenic plasma shows increased incorporation. This effect is the same as is found with the flow cytometry assay used in Examples 1, 2 and 3 in which the number and ploidy of megakaryocytes each rose with increasing amounts of thrombocytopenic plasma but failed to rise with the addition of normal plasma. The same concordance of the serotonin and flow cytometer assays was observed with purified sheep megapoietin.

The serotonin and flow cytometer assays have proven to be specific for MP activity and show little stimulation in response to any other known cytokine. The known cytokines were tested at concentrations which ranged from 1/100 the concentration of the known $ED_{50}$ (effective dose for 50% of biological effect) to 1000 times the concentration of the known $ED_{50}$. The cytokines enumerated in Table 4 have been tested for activity in rat liquid bone marrow culture system. The effects on the number of nucleated cells, number of megakaryocytes and ploidy were taken from flow cytometer assays and the rest by serotonin assays. As can be seen from the table, MP shows major stimulation while erythropoietin shows minor stimulation. IL-6 shows a slight effect on the number of megakaryocytes, recombinant rat IL-3 shows slight effect on megakaryocyte number and ploidy (but only in the presence of Nutricyte), and recombinant murine stem cell factor shows a barely detectable increase in serotonin incorporation.

TABLE 4

| Cytokine | #nucleated cells | #Megakaryocytes | Mean ploidy | Serotonin |
|---|---|---|---|---|
| nml rat plasma | 0+ | 0+ | 0+ | 0+ |
| tc rat plasma | 0+ | 5+ | 5+ | 5+ |
| nml rab.plasma | 0+ | 0+ | 0+ | 0 |
| tc rab plasma | 0+ | 5+ | 5+ | 5+ |
| mml sheep pl | 0+ | 0+ | 0+ | 0+ |
| pure mp | 0+ | 5+ | 5+ | 5+ |
| tc sheep pl | 0+ | 5+ | 5+ | 5+ |
| rech EPO | 2+ | 2+ | 2+ | 2+ |
| r mur SCF | NT | NT | NT | 1+ |
| r rat IL-3 | 5+ | 0+ | 0+ | NT |
| nutricyte | 5+ | 1+ | 1+ | NT |
| r h IL-6 | 3+ | 1+ | 0+ | NT |
| r mur GMCSF | 5+ | 0+ | 0+ | NT |
| pur murGMCSF | 5+ | 0+ | 0+ | NT |
| pur h plt PDGF | 0+ | 0+ | 0+ | NT |
| r h IL-3 | 0+ | 0+ | 0+ | NT |
| r h IL-1a | 0+ | 0+ | 0+ | NT |
| mur pur EGF | 0+ | 0+ | 0+ | NT |
| rhMCSF | 4+ | 0+ | 0+ | NT |
| rhTNFa | 2+ | 0+ | 0+ | NT |
| r h IF-gamma | 0+ | 0+ | 0+ | NT |

TABLE 4-continued

| Cytokine | #nucleated cells | #Megakaryocytes | Mean ploidy | Serotonin |
|---|---|---|---|---|
| acid bov FGF | 0+ | 0+ | 0+ | NT |
| r h IL-11 | NT | NT | NT | 0+ |
| r mur LIF | NT | NT | NT | 0+ |
| r mur TNFA | NT | NT | NT | 0+ |
| rat plt TGFB1 | inh | inh | inh | NT |
| h pltTGFB1 | inh | inh | inh | NT |
| HEKCM | inh | inh | inh | NT |

[All graded on scale of 0+ (no activity) to 5+ (maximal activity)]
[NT = not tested, inh = inhibits assay]

EXAMPLE 5

Purification of Megapoietin

Prior to purification, megapoietin was tested and found to have the following general biochemical characteristics:

1. Activity completely destroyed by trypsin and 2% SDS

| 2. | Activity stable in: | 0.1% TFA |
| | | 50 mM KHPO4 |
| | | 0.8M NaPO$_4$/0.1% TFA |
| | | 2M Urea |
| | | buffers with pH from 4 to 9.0 |

3. Activity completely destroyed by 10 min at 100 C 72% of activity retained after 1 h at 37 C
4. 66% recovery of activity after lyophilization
5. 2-mercaptoethanol destroys 75–80% of activity
6. 25% acetic acid destroys 75% of activity after 1 h
7. 2M urea and 25% acetic acid together destroy 42% of activity
8. 90–100% of activity is precipitated from plasma by 20–50% concentration range of ammonium sulfate at 4 C
9. Between polyethylene glycol (PEG, MW=3350) concentrations of 7.5 and 15% (w/w) 100% of activity is precipitated from plasma.
10. MP is subject to marked aggregation and as such is retained by 3500, 14,000 MWCO dialysis bags as well as 10,000, 30,000 and 100,000 MWCO Centricon membranes and also sometimes by 0.45 um Millipore filters. Aggregation is ameliorated and activity preserved in the following detergents (presented in descending order of effectiveness in preventing aggregation): Triton X100=Tween 20>CHAPS>Octylglucoside>NP40. To minimize aggregation, 2.5% CHAPS is routinely added to the preparation after the DEAE chromatography.

Megapoietin has been isolated from thrombocytopenic serum using a nine step purification scheme, essentially comprised of:

1. PEG precipitation
2. CM Sepharose chromatography twice
3. DEAE Sepharose chromatography
4. Hydroxylapatite chromatography twice
5. Mono S chromotography
6. WGA sepharose chromatography
7. Heparin sepharose chromatography
8. TMS reverse phase HPLC
9. TSK HPLC Each of the steps are described in detail below.

1. Peg Precipitation

Frozen plasma was thawed overnight. Any clot was removed by 15 min centrifugation at 5000 g at 4° C. Supernant plasma was pooled and mixed with ⅕th its volume of 42.5% (w/w) polyethylene glycol (MW=3350) to attain a final concentration of 7.5%. Suspension was stirred at 4° C. for 1 hour and the precipitate (containing most of the fibrinogen) was centrifuged at 5000 × g for ½ h and the supernatant decanted. The pooled supernatants were then diluted with an equal volume of 50 mM NaPO$_4$ pH 6.0 and titrated with concentrated phosphoric acid to obtain a final pH of 6 (at 4° C.).

2. CM Sephrose Chromatography (using FPLC)

CM 1 Step

A CM Sepharose FF column containing 8 L bed volume was equilibrated with 50 mM NaCl, 50 mM NaPO$_4$, pH 6.0 (Buffer IA) and approximately 45 L of PEG product loaded at 4.5 L/h. The column was then washed with 20–24 L of Buffer IA and then eluted with 4–5 L of Buffer IB (300 mM NaCl, 50 mM NaPO$_4$, pH 6.0). The eluted material was concentrated to 1.5 L and diafiltered vs. Buffer IA using the Amicon CH2 spiral cartridge system.

CM 2 Step

A 1 liter bed volume CM Sepharose FF column was equilibrated with Buffer IA and approximately 1.5 L of CM1 product loaded at 10 ml/min. The column is washed with 2.5 L of Buffer IA and then eluted with a 5 L linear gradient starting at 100% Buffer IA and ending with 50% Buffer IC (500 mM NaCl, 50 mM NaPO4, pH 6.0):50% Buffer IA. Fractions were collected and assayed for MP activity. Usually activity was eluted between 25% and 46% Buffer IC as two or three broad peaks.

Fractions containing activity were pooled, concentrated to approximately 500 mL and diafiltered into Buffer IIA using the Amicon CH2 Spiral Cartridge System.

3. DEAE Sepharose Chromatography

In initial experiments. MP was found to bind to DEAE under the conditions below and in analytical runs showed a single activity peak from 8.5 to 9.7% Buffer IIB. In preparative runs, several activity peaks eluted over a wider salt concentration and considerable amounts of aggregated material appeared in the flow through.

450 mL DEAE Sepharose FF column was equilibrated with Buffer IIA (20 mM NaCl, 20 mM Tris pit 8.6) and approximately 500 ml of the CM2 product applied at 10 mL/min. The column was then washed with 900 mL of IIA and then eluted with a 3600 mL linear gradient starting at 2.5% Buffer IIB(1000 mM NaCl, 20 mM Tris pH 8.6):97.5% Buffer IIA and ending at 17.5% Buffer IIB:82.5% Buffer IIA. Fractions were collected and assayed for MP. MP usually eluted as two or three discrete peaks starting at 8.5% Buffer IIB and ending at 12.5% Buffer IIB. Peak fractions were pooled, concentrated to approximately 150–200 ml with the Amicon CH2 Spiral Cartridge System and subsequently under $N_2$ pressure with a Amicon stirred cell using the PM 10 membrane. Any precipitate was removed by centrifugation at 5000 × g and the solution made to 0.25% in CHAPS, aliquotted into usually 6×150 mg portions and frozen at -84 C. At this step approximately 66% of the total activity remained in the column flow-through because of aggregation.

4. Hydroxylapatite Chromatography

This step was based on a preliminary experiment that showed that at moderate NaCl concentration and low phosphate concentration, the activity failed to bind to the HA matrix and flowed through the column, giving a high purification factor. Subsequently, it was found that by reapplying the material at lower NaCl concentration, it bound and further purification could be achieved.

HA1 Step

A custom made 19 mm × 10 cm HA column (bed volume=28 ml) was obtained from Bio-Rad and equilibrated with Buffer IIIA(100 mM NaCl, 10 mM $KPO_4$ pH 6.8, 0.25% CHAPS) at 4° C. Each 150 mg (35–40 ml) aliquot DEAE product was applied to the column at 2.5 ml/min. and the column washed with Buffer IIIA for approximately 90 mL of ILIA. The flow-through (FT) was collected and contained almost all of the activity. The FT for six HA1 FT runs were pooled, concentrated using a stirred Amicon cell (YM10 membrane) to approximately 40–50 ml and then dialyzed vs 4 volumes of 10 mM $KPO_4$ pH 6.8 containing 0.25% CHAPS and no NaCl to prepare sample that was at a final concentration of 20 mM NaCl, 10 mM $KPO_4$ pH 6.8 and 0.25% CHAPS.

HA2 Step

A BioRad HA column containing the same resin as above but in a format of 7.8 mm × 10 cm (bed volume approx 4.8 ml) was equilibrated with Buffer IIIA-low (Same as IIIA but containing only 20 mM NaCl) and the sample (approx 40–50ml) was applied at a flow rate of 0.5 ml/min. The column was washed with Buffer IIA-low until the OD returned to baseline. The adherent protein was step-eluted with Buffer IIIB (20 mM NaCl, 180 mM $KPO_4$, pit 6.8, 0.25% CHAPS) and contained most of the activity in approximately 4 ml.

5. Mono S Chromatography

Like CM, Mono S was found in preliminary experiments to bind MP and was employed here to perform a high resolution cation exchange separation.

A 5 mm × 5 cm (1 ml bed volumn) Mono S column was obtained from Pharmacia and equilibrated with Buffer IV A (50 mM NaCl, 50 mM $KPO_4$, pH 6). The HA2 sample (in 20 mM NaCl, 0.180 mM $KPO_4$, pH 6.8) was diluted by the addition of two volumes of 20 mM NaCl, 0.028M $H_3PO_4$, 0.25% CHAPS to yield a final concentration of approximately 20 mM NaCl 79 mM $KPO_4$, pH 6.0. This specimen (approx 12 ml) was loaded at 0.5 ml/min at 4 C and then washed with 1–2 ml of Buffer IVA. A 24 ml linear gradient starting with 0% Buffer IVB (500 mM NaCl, 50 mM $KPO_4$ pH 6.0) 100% Buffer IVA and ending with 60% Buffer IVB 40% Buffer IVA was run and 36 fractions collected. These were assayed for MP activity and peak fractions pooled (4–5 ml). Activity eluted as a single broad peak between 19% and 31% IVB.

6. Wga Sepharose Chromatography

Preliminary experiments showed that all of the MP bound to wheat germ agglutinin (WGA), some weakly and some more strongly. This suggests that megapoietin is a glycoprotein. The former material usually Fluted in the wash during most preparations. The more tightly bound material was selected for subsequent purification.

The 4–5 ml Mono S pool was brought to a concentration of 0.5M NaCl by the addition of solid NaCl and then had its pH adjusted by the addition of 60 μL/ml of a solution containing 0.5M dibasic $NaPO_4$ and 0.5M NaOH to yield a solution that was 0.5M NaCl, 50 mM $NAPO_4$, pH 7.5.

A column containing 1 ml of WGA-Sepharose 6MB (obtained from Pharmacia) was equilibrated with Buffer V (0.5M NaCl, 50 mM NaPO4, pH 7.5, 0.25% CHAPS). The sample was loaded at 2 ml/hour over 2.5 h and then washed with 5 column volumes of Buffer V. The column was then eluted with 0.66 column volume of Buffer V-B (same as V but with only 0.125M NaCl) and then with 1.5 column volumes of chitodiose (4 mg/ml in V-B). The eluate contained most of the activity in 1.5–2 ml.

7. Heparin Sepharose

Initial purification attempts showed a persistent 56,000 MW protein that was sequenced and Found to be Protein C inhibitor. Since this protein was known to bind tightly to heparin sepharose, a heparin sepharose separation step was employed specifically to remove this contaminant.

The WGA eluate was diluted with ¼ volume of 0.25% CHAPS in water to give a final concentration of 100 mM NaCl, 40 mM $NaPO_4$ pH 7.5, 0.25% CHAPS.

Heparin Sepharose was obtained from Pharmacia and a 1 ml column was prepared and equilibrated with Buffer VI-A (100 mM NaCl, 25 mM $NaPO_4$ pH 7.5, 0.25% CHAPS). The 2.5 ml sample was loaded at 2 ml/h and then washed with 1.5 ml Buffer VI-A. The column was eluted with a 12 mL linear gradient starting at 0% Buffer VI-B (0.6 M Na Cl, 25 mM $NaPO_4$ pH 7.5, 0.25% CHAPS): 100% Buffer VI-A and ending at 100% Buffer VI-B. 0.5 mL fractions were collected and assayed for activity. Activity usually eluted as a broad peak, from 180 to 300 mM NaCl. Peak fractions were pooled (approx 2–3 ml) and frozen prior to running on TMS reverse phase chromatography.

8. TMS Reverse Phase Chromatography

Initial experiments showed that MP bound tightly to hydrophobic matrices (C-18, C-8) and could not be removed with solvents which still preserved activity. A less hydrophobic matrix which still bound MP tightly was therefore chosen to allow its removal with reagents that preserved activity.

A TMS column, 7.8 mm × 7.5 cm (TosoHaas) was equilibrated with 90% VII-A (0.1% TFA in water): 10% VII-B (0.085% TFA in 75% acetonitrile, 25% isopropanol). The Heparin Sepharose product was titrated with 40 μL/ml of 1.125M $HPO_4$ and applied to the column with multiple 0.5 ml injections (up to a total of six injections). The column was washed to the baseline OD value with 90% VII-A: 10% VII-B and then eluted at 0.5 ml/min. with a linear 15 ml gradient starting from 90% VII-A: 10% VII-B and ending at 30% VII-A: 70% VII-B. 0.2 ml fractions were collected and assayed. Peak activity eluted over 2 to 4 fractions at 31.8 to 33 minutes (50–52.5% VII-A).

9. TSK Chromatography

To remove the few remaining higher molecular weight contaminants, a sizing step was performed as the last step of the purification. In order to prevent irreversible adsorption to the TSK matrix, the separation was run under reverse phase elution conditions.

A TSK G3000 SW column (7.5 mm × 60 cm) (TosoHaas) was equilibrated with 50% VII-A: 50% VII-B. Approximately 0.3–0.4 ml of reverse phase product was applied and the column eluted isocratically at 0.5 ml/min with 50% VII-A: 50% VII-B. The active fractions eluted at 25 to 29 minutes of elution. The following Table 5 provides a summary of purification recoveries.

TABLE 5

Summary of Purification Recoveries

| | Volume (mL) ±SD | Protein Conc (mg/mL) ±SD | Total Protein (mg) ±SD | Act (U/mL) ±SD | Total Act ±SD | Recovery (%) ±SD | SA ±SD | PF ±SD |
|---|---|---|---|---|---|---|---|---|
| Plasma | 21112 | 48.4 | 1023000 | 0.022 | 502 | 100 | 0.0005 | 1 |
| | 918 | 7.8 | 155200 | 0.01 | 200 | | 0.0003 | |
| PEG ppt | 49344 | 12.4 | 609393 | 0.0107 | 537 | 100 | 0.0009 | 1.69 |
| (Step 1) | 2098 | 1.4 | 61495 | 0.0062 | 296 | 27 | 0.0006 | 0.51 |
| CM1 Eluate | 3636 | 7.73 | 24656 | 0.143 | 514 | 96 | 0.02 | 4.0 |
| (Step 2.1) | 1705 | 3.11 | 6742 | 0.061 | 306 | 30 | 0.009 | 9 |
| CM2 Eluate | 2437 | 3.29 | 7880 | 0.182 | 425 | 89 | 0.054 | 115 |
| (Step 2.2) | 276 | 0.31 | 932 | 0.091 | 166 | 16 | 0.026 | 35 |
| CM2 Eluate | 524 | 13.4 | 6999 | 1 | 477 | 102 | 0.069 | 152 |
| (Conc) | 5 | 1.9 | 965 | | 105 | 26 | 0.018 | 50 |
| DEAE | 1039 | 1.066 | 1109 | 0.141 | 145 | 31 | 0.134 | 292 |
| Eluate | 69 | 0.116 | 141 | 0.037 | 32 | 9 | 0.037 | 95 |
| (Step 3) | | | | | | | | |
| DEAE | 150 | 6.85 | 875 | 0.725 | 117 | 26 | 0.133 | 311 |
| Eluate | 58 | 3.25 | 177 | 0.231 | 51 | 9 | 0.051 | 82 |
| (Conc) | | | | | | | | |
| HA1 FT | 355 | 0.0367 | 12.9 | 0.346 | 124 | 28 | 9.41 | 23084 |
| (Step 4.1) | 56 | 0.0057 | 3.2 | 0.16 | 61 | 12 | 3.78 | 7978 |
| HA2 Eluate | 9.92 | 0.652 | 3.68 | 11.8 | 84.2 | 16.2 | 21.17 | 40829 |
| (Step 4.2) | 10.9 | 0.363 | 0.96 | 10.5 | 35.4 | 4.5 | 9.31 | 11660 |
| Mono S | 5.34 | 0.119 | 0.436 | 10.55 | 55.1 | 11.9 | 80 | 187374 |
| Eluate | 2.23 | 0.046 | 0.03 | 3.08 | 36 | 8.3 | 23 | 69038 |
| (Step 5) | | | | | | | | |
| WGA Eluate | 1.42 | 0.092 | 0.12 | 10.71 | 26.2 | 5.43 | 274 | 458068 |
| (Step 6) | 0.32 | 0.009 | 0.023 | 10.69 | 15.8 | 1.37 | 60 | 19568 |
| Hep S | 1.25 | | 19.2 | 2.4 | 4.8 | | | |
| Eluate | | | | | | | | |
| (Step 7) | | | | | | | | |
| TMS RPC | 0.16 | | 0.004 | 57.5 | 9.2 | 3.44 | 1785 | 4973039 |
| Eluate | | 0 | | | 2.32 | 728 | 777763 | |
| (Step 8) | | | | | | | | |
| TSK Eluate | 3 | | 0.0017 | | 7.95 | 1.6 | 4518 | 9035294 |
| (Step 9) | | | | | | | | |

Characterization of Final TSK Product

The final TSK peak contained approximately 1–2 micrograms of protein. After iodination, the purified product ran on SDS gels (Laemmli system, no reduction) as a major band with MW approximately 28,000. Under identical conditions of electrophoresis, the SDS gels of native (not-iodinated) TSK product have been sliced, eluted and the activity localized to the same 28,000 MW band. When reduced with DTT and run on SDS gels, the major band had a MW of approximately 31,000.

The final TSK peak containing 2 micrograms recovered 1–2% of the starting activity for a final purification factor of greater than 9,000,000.

A control purification protocol (through steps 2 and 3, the CM and DEAE steps above) was carried out on 40 liters of plasma obtained from normal (i.e., non-thrombocytopenic sheep). At no time was any activity found in the elution chromatograms of either the CM or DEAE steps. The DEAE step gave a 30 fold concentration of activity, which suggested that normal plasma contained less than 1/30th of the level of MP in thrombocytopenic plasma and was below the detection limit of the assays.

EXAMPLE 6

Isolation of DNA Encoding Human Megapoietin

Determination of MP Amino Acid Sequence

Megapoietin purified to homogeneity or megapoietin from a late step of the purification scheme, electrophoresed on SDS polyacrylamide gel and electro-transferred to nitrocellulose or polyvinylidene fluoride (PVDF) membrane can be subjected to enzymatic digestion with trypsin and/or endoproteinase Lys-C. The resulting peptides could be separated by reverse phase chromatography on a Hewlett-Packard 1090M HPLC system employing a Vydac 214TP52 column. Individual peptides could be sequenced on an Applied Biosystems 477A protein sequencer and 120A analyzer.

Identification and Isolation of MP cDNA and Gene

Coding DNA sequences (sense and antisense) implied by amino acid sequences determined from MP peptides can be synthesized on an Applied Biosystems model 370B DNA synthesizer employing β-cyanoethyl phosphoramidite chemistry. These oligonucleotides are to be used as hybridization probes or in pairs as PCR primers against various DNA targets.

mRNA isolated from human tissue containing megapoietin protein can be used to synthesize cDNA employing reverse transcriptase and standard techniques. Resulting cDNA can be used to construct a cDNA library in a vector such as lambda ZAP Express (Stratagene). This library can then be screened for hybridization with one or more of the synthetic DNA probes. Additionally, various pairs of sense and anti-sense synthetic DNA can be used as PCR primers for amplification of various regions of cDNA. Product DNA can be authenticated by sequencing and demonstrating that it predicts the amino acid sequence adjacent to that used to generate the primer sequence and can then be used as a hybridization probe in the screening of cDNA and genomic DNA libraries.

A human genomic DNA library can be screened with cDNA probes or DNA probes synthesized from the determined amino acid sequence of the megapoietin protein to obtain the megapoietin gene.

the third and fourth columns for Day 4. Compared with the simultaneous buffer controls, there was no stimulation of megakaryocyte number, ploidy or platelet count.

TABLE 6

|  | Normal Rats | 2 DAY INJECT | | 4 DAY INJECT | | 4 DAY INJECT | |
| --- | --- | --- | --- | --- | --- | --- | --- |
|  |  | Buffer n = 4 | DE-TC n = 4. | Buffer n = 5 | DE-TC n = 2 | Buffer n = 5 | DE-N n = 4 |
| % M | 0.094 +/− 0.032 | 0.128 0.029 | 0.097 0.034 | 0.128 0.005 | 0.159 0.023 | 0.127 0.020 | 0.133 0.016 |
| 8N | 18.41 +/− 6.38 | 18.17 5.35 | 15.20 2.93 | 15.45 1.65 | 8.32 1.41 | 12.61 1.53 | 10.79 2.39 |
| 16N | 64.08 +/− 4.57 | 59.85 1.15 | 39.24 3.29 | 63.11 3.10 | 26.58 5.34 | 52.25 8.01 | 50.03 5.90 |
| 32N | 17.34 +/− 7.00 | 20.41 5.90 | 40.25 3.07 | 20.59 2.59 | 53.40 2.30 | 33.83 9.58 | 38.44 7.22 |
| 64N | 0.31 +/− 0.37 | 1.57 0.74 | 4.73 2.18 | 0.86 0.29 | 11.71 4.44 | 0.70 0.34 | 0.74 0.31 |
| Mean Ploidy | 16.09 +/− 1.56 | 16.97 0.83 | 20.35 1.10 | 16.75 0.45 | 25.77 2.24 | 18.48 1.85 | 19.61 1.27 |
| Plt Ct (tail) | *1.402 +/− 0.101 | 1.518 0.147 | 1.564 0.244 | 1.300 0.148 | 1.952 0.129 | 1.383 0.064 | 1.401 0.101 |
| WBC (tail) | **17.43 +/− 5.11 | 11.32 1.45 | 9.61 2.32 | 18.83 3.07 | 14.75 0.04 | 17.52 3.89 | 19.63 0.81 |
| HCT | **38.80 +/− 0.60 | 39.10 1.40 | 40.10 1.20 | 39.80 0.90 | 40.20 2.50 | 36.70 0.50 | 36.30 2.00 |

Nominal rats = 365 total
**tail vein platelet counts at Day 0
**tail vein counts of rats for 4 Day Injection

EXAMPLE 7

Bioactivity of Purified Megapoietin in Vivo

To determine whether MP had any biological activity, partially purified MP (DE-TC, purified from thrombocytopenic sheep plasma through the DEAE step; purification factor=×30) was tested and compared with buffer or partially normal sheep plasma (DE-N, purified from normal sheep plasma through the DEAE step and which contained no detectable activity in vitro). The following Table 6 summarizes the data from three sets of animal injections. All animals were male. 220–330 g rats.

The first series of injections were a comparison of DE-TC vs Buffer injected every 12 h for 4 injections and the animals harvested 12 hours after the last injection [on Day 3 (data listed under 2 Day Injections in Table 6)]. Them was no change in the platelet count but a large and statistically significant shift in megakaryocyte ploidy with the Mean Ploidy rising from 16.97 to 20.35.

In a second series of animals, injections of DE-TC or Buffer of the same amount as in the first series were administered every 12 h for 8 injections and the animals harvested on Day 5 (results listed under the first two columns for 4 Day Injections below). These show even more stimulation of megakaryocyte ploidy and a small (but statistically significant) rise in the number of megakaryocytes. Furthermore, the platelet count of DE-TC animals showed a statistically significant rise (p<0.001 ) compared to Buffer. Buffer injected animals showed no difference from uninjected littermates.

To exclude a non-specific stimulatory effect from sheep protein, normal sheep plasma was purified to the same extent and along with buffer controls was injected in a third series of animals in the same amount and for the same extent (every 12 h for 8 injections). The data is shown below under For animals sacrificed on Day 3 after 2 days of injections or on Day 5 after 4 days of injections, plasma samples obtained at sacrifice were tested in the MP assay (serotonin incorporation) and found to have no stimulatory activity.

To confirm the stimulatory effect of MP on the platelet count in vivo, a second preparation of MP (again purified to the same extent as that used above, but with approximately half the total activity) was injected every 12 h for 8 injections (2 rats) and the platelet count of these and two buffer injected control animals followed daily. The platelet count of the MP-injected animals began to rise 24 hours after the completion of the injections and rose to a maximum of $2.05 \times 10^9$/ L on Day 8 and then returned to the values of control animals by Day 16.

These results may be summarized as showing that MP injection produced increased megakaryocyte ploidy in vivo that was readily apparent after two days and the ploidy was maximal after 4 days of injection. After four days of injection the number of megakaryocytes also increased. Following the rise in megakaryocyte number and ploidy at four days, there was a gradual rise in the platelet count which reflected a stimulated rate of platelet production.

EXAMPLE 8

Bioactivity of Human Megapoietin

As was shown for thrombocytopenic plasma obtained from busulfan-treated rats, rabbits and sheep, thrombocytopenic plasma obtained from busulfan-treated human bone marrow transplant patients was also found to stimulate the assay for MP. The assay response obtained using plasma from three such patients is shown below in Table 7.

TABLE 7

| | | Platelets (per mm³) | Assay (cpm) |
|---|---|---|---|
| Patient #1 | Day 0 | 197,000 | 6006 |
| | Day 13 | 32,000 | 8040 |
| | Day 14 (after platelet transfusion) | 40,000 | 6137 |
| Patient #2 | Day 0 | 267,000 | 6752 +/− 130 |
| | Day 17 | 31,000 | 8033 +/− 392 |
| Patient #3 | Day 0 | 198,000 | 6198 +/− 336 |
| | Day 8 | 17,000 | 6934 +/− 316 |
| TC Sheep plasma | Control | | 20,547 |

EXAMPLE 9

Ability of MP to Increase Shelf-Life of Platelets

In addition to stimulating production of platelets from megakaryocytes, MP has been found to promote platelet survival in vitro. Normal human platelets have a "shelf-life" of approximately 5 days before becoming inactive. MP may significantly prolong the survival and viability of platelets during storage and therefore improve the supply of this product. The effect of MP on rat platelet survival has been investigated. In vitro rat platelet rich plasma was obtained from citrated blood and stored at room temperature for three days. The viability of platelets over that period of time was then assessed by measuring the uptake of radioactive serotonin and the stimulation of its release by the calcium ionophore A23187. As shown below in Table 8, the addition of MP to the platelet suspension increased platelet survival from 3% (in the absence of MP) to 28% (in its presence), a 9-fold increase.

TABLE 8

| Time (h) | Serotonin Type | Serotonin Release |
|---|---|---|
| 0 | 94% | 100% |
| 15 | 82% | 73% |
| 48 (−MP) | 3% | 54% |
| 48 (+MP) | 28% | 50% |

EXAMPLE 10

MP Binds to Platelets

Figure 3:
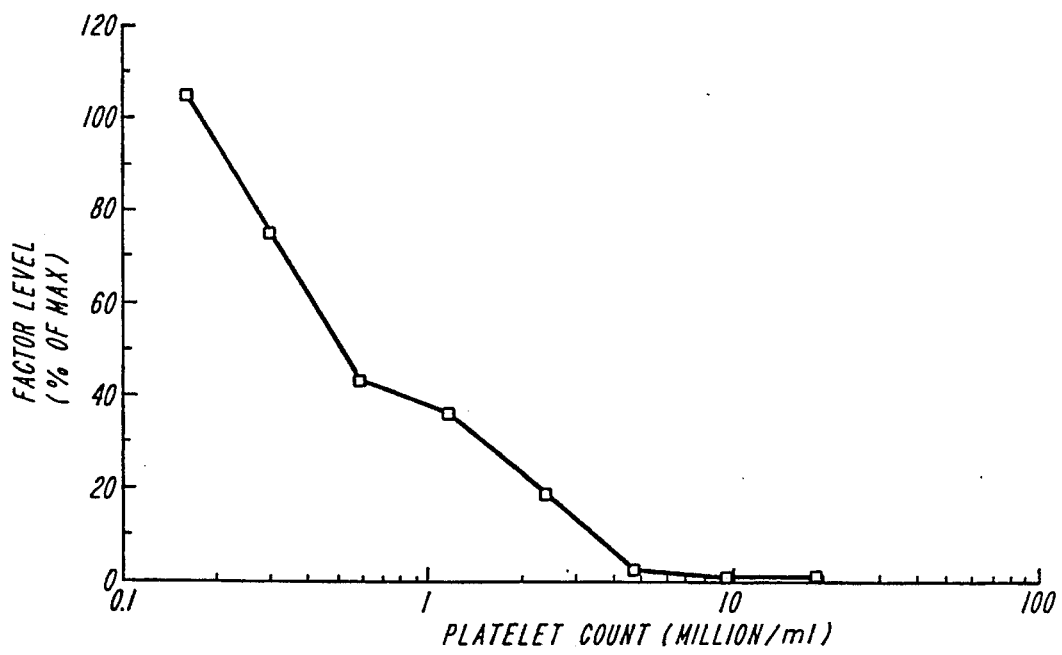
FIG. 3 is a graph plotting megapoietin activity (% of maximum) in the presence of increasing amounts of platelets.

Platelets bind to and metabolize MP. This is the basis for a novel feedback-loop. This process is temperature-dependent and proportional to the log [platelet]. The graph presented as FIG. 3 summarizes this effect. Rat platelets were added to buffer containing 15% rabbit plasma-derived serum (to maintain cell viability and to serve as a carrier for the added MP) doped with several femtograms of MP. After incubation for 1 h at room temperature, the platelets were centrifuged and the MP activity remaining quantitated by the serotonin assay. This data supports the role of the platelet itself in determining the circulating concentration of its own regulatory cytokine. Moreover it predicts the presence on the platelet surface of a megapoietin receptor and the possibility to modulate the effect of that receptor by a megapoietin antagonist or other small molecule (e.g.,vincristine). Megapoietin was found to bind tightly to a platelet receptor. The receptor on platelets for MP appeared to be present in relatively small numbers as is common for cytokines. In contrast, the receptor for MPL has been reported to be present in large numbers approximately equal to the number (20,000–40,000) of platelet GpIIa/IIIb receptors.

Equivalents

Those skilled in the art will recognize, or be able to ascertain using no more than routine experimentation, numerous equivalents to the specific embodiments of the invention specifically described herein. Such equivalents are intended to be encompassed in the scope of the following claims.

We claim:

1. A method for prolonging the survival and viability of a platelet containing preparation comprising contacting the preparation with an effective amount of a megapoietin protein, said protein being capable of: i) stimulating an increase in the megakaryocyte size, number and ploidy as well as production of platelets therefrom; and ii) binding to platelets in vitro or in vivo.

2. A method of claim 1, wherein the survival and viability of the platelet containing preparation is determined as an increased uptake of serotonin or a stimulation of serotonin release by the calcium ionophore A23187 in an in vitro serotonin uptake assay or as an increased number of platelets in a flow cytometry assay.

3. A method according to claim 1, herein the platelet containing preparation is whole blood.

4. A method according to claim 1, wherein the platelet containing preparation is a preparation containing solely platelets and substantially free of other blood components.

* * * * *

UNITED STATES PATENT AND TRADEMARK OFFICE
CERTIFICATE OF CORRECTION

PATENT NO. : 5,571,686
DATED : November 5, 1996
INVENTOR(S) : Robert D. Rosenberg, David J. Kuter and David Beeler It is certified that error appears in the above-identified patent and that said Letters Patent is hereby corrected as shown below:

Claim 1, should read --

1. A method for prolonging the survival and viability of a platelet containing preparation comprising contacting the preparation with an effective amount of a megapoietin protein, <u>wherein the megapoietin protein is about 31 kd as determined by SDS gel electrophoresis under reducing conditions and is about 28 kd under nonreducing conditions,</u> said protein being capable of: i) stimulating an increase in the megakaryocyte size, number and ploidy as well as production of platelets therefrom; and ii) binding to platelets in vitro or in vivo. --.

Signed and Sealed this

Seventh Day of November, 2000

Attest:

Q. TODD DICKINSON

*Attesting Officer*  *Director of Patents and Trademarks*